US010532109B2

(12) United States Patent
Chen et al.

(10) Patent No.: US 10,532,109 B2
(45) Date of Patent: Jan. 14, 2020

(54) PEPTIDE-DNA CHIMERAS FOR TREATMENT OF HER OVEREXPRESSING CANCERS

(71) Applicant: ARIZONA BOARD OF REGENTS ON BEHALF OF ARIZONA STATE UNIVERSITY, Scottsdale, AZ (US)

(72) Inventors: Shengxi Chen, Chandler, AZ (US); Yanmin Zhang, Tempe, AZ (US); Sidney Hecht, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/301,888

(22) PCT Filed: May 8, 2017

(86) PCT No.: PCT/US2017/031548
§ 371 (c)(1),
(2) Date: Nov. 15, 2018

(87) PCT Pub. No.: WO2017/200787
PCT Pub. Date: Nov. 23, 2017

(65) Prior Publication Data

US 2019/0282706 A1 Sep. 19, 2019

Related U.S. Application Data

(60) Provisional application No. 62/338,000, filed on May 18, 2016.

(51) Int. Cl.

| | |
|---|---|
| ***A61K 47/68*** | (2017.01) |
| ***A61K 38/16*** | (2006.01) |
| ***C07K 14/31*** | (2006.01) |
| ***C07K 16/32*** | (2006.01) |
| ***C07K 16/30*** | (2006.01) |

(52) U.S. Cl.
CPC .......... *A61K 47/6851* (2017.08); *A61K 38/16* (2013.01); *A61K 47/6807* (2017.08); *C07K 14/31* (2013.01); *C07K 16/30* (2013.01); *C07K 16/32* (2013.01); *C07K 2317/73* (2013.01); *C07K 2318/20* (2013.01)

(58) Field of Classification Search
None
See application file for complete search history.

(56) References Cited

U.S. PATENT DOCUMENTS 9,040,287 B2* 5/2015 Chang .................. C12Q 1/6818 435/287.2
10,159,760 B2* 12/2018 Syud ...................... C07K 14/71
2003/0104045 A1 6/2003 Virtanen et al.
2009/0227774 A1* 9/2009 Turberfield ............ C12N 15/10 530/358
2012/0165650 A1 6/2012 Syud et al.
2017/0028070 A1* 2/2017 Hah .................. G01N 33/5308
2019/0106396 A1 4/2019 Chen

FOREIGN PATENT DOCUMENTS

WO 200101748 1/2001
WO WO2007122405 A1 11/2007
WO WO 2015/102316 * 7/2015
WO WO2015105926 A1 7/2015

OTHER PUBLICATIONS

Alavizadeh et al., 'Improved Therapeutic Activity of HER2 Affibody-Targeted Cisplatin Liposomes in HERs-Expressing Breast Tumor Models' Expert Opinion on Drug Delivery, vol. 159, No. 4, pp. 1-36(2015).
Alexis et al., 'HER-2 Targeted Nanoparticle-Affibody Bioconjugates for CancerTherapy' ChemMedChem, pp. 1-11 (Dec. 5, 2012).
Eigenbrot et al., 'Structural Basis for High-Affinity HER2 Receptor Binding by an Engineered Protein' PNAS, vol. 107, pp. 15039-15044 (2010).
International Search Report from Parent PCT No. PCT/US2017/031548, dated Oct. 17, 2017, 25 pages.
Agudelo, D., et al (2014). Intercalation of antitumor drug doxorubicin and its analogue by DNA duplex: structural features and biological implications. International journal of biological macromolecules, 66, 144-150.
Arteaga, C. L., et al. (2012). Treatment of HER2-positive breast cancer: current status and future perspectives. Nat. Rev. Clin. Oncol. 9, 16-32.
Berezov, A., et al (2001). Disabling erbB receptors with rationally designed exocyclic mimetics of antibodies: structure-function analysis. J. Med. Chem. 44, 2565-74.
Cappuzzo, F., et al (2006). HER2 mutation and response to trastuzumab therapy in non-small-cell lung cancer. N. Engl. J. Med. 354, 2619-2621.
Chen, S. et al. "Detection of dihydrofolate reductase conformational change by FRET using two fluorescent amino acids." Journal of the American Chemical Society 135.35 (2013): 12924-12927.
Chen, S. et al. "p-Thiophenylalanine-induced DNA cleavage and religation activity of a modified vaccinia topoisomerase IB." Biochemistry50.43 (2011): 9340-9351.

(Continued)

*Primary Examiner* — Laura B Goddard

(74) *Attorney, Agent, or Firm* — Quarles & Brady LLP; Jessica L. Lewis

(57) ABSTRACT

Provided herein are therapeutic agents having specificity for having inhibitory activity against cancer cells that overexpress human epidermal growth factor receptor (HER) genes, including therapeutic agents comprising one or more HER-targeting peptides, pharmaceutical compositions comprising such therapeutic agents, and methods of using such compositions to treat or prevent a cancer or other disease condition associated with HER overexpression.

3 Claims, 19 Drawing Sheets

Specification includes a Sequence Listing.

(56) References Cited

OTHER PUBLICATIONS

Chen, S. et al. "Synthesis of pdCpAs and transfer RNAs activated with derivatives of aspartic acid and cysteine." Bioorganic & medicinal chemistry 16.19 (2008): 9023-9031.
Chen, S. et al. "Two pyrenylalanines in dihydrofolate reductase form an excimer enabling the study of protein lynamics." Journal of the American Chemical Society 134.46 (2012): 18883-18885.
Dou, S., et al. "A feasible approach to evaluate the relative reactivity of NHS-ester activated group with primary amine-derivatized DNA analogue and non-derivatized impurity." Nucleosides, Nucleotides and Nucleic Acids 34.2 (2015): 69-78.
Erben, C. M., et al (2006). Single-molecule protein encapsulation in a rigid DNA cage. Angewandte Chemie International Edition, 45(44), 7414-7417.
Gschwind, A., et al (2004). The discovery of receptor tyrosine kinases: targets for cancer therapy. Nat. Rev. Cancer 4, 361-370.
Hellstrom, I., et al (2001). Overexpression of HER-2 in ovarian carcinomas. Cancer Res. 61, 2420-2423.
Jahanzeb, M. (2008). Adjuvant trastuzumab therapy for HER2-positive breast cancer. Clin. Breast Cancer 8, 324-333.
Lambert, J. M., et al (2014). Ado-trastuzumab Emtansine (T-DM1): an antibody-drug conjugate (ADC) for HER2-positive breast cancer. J. Med. Chem. 57, 6949-6964.
Nord, K., et al (1997). Binding proteins selected from combinatorial libraries of an a-helical bacterial receptor domain. Nat. Biotechnol. 15, 772-777.
Orlova, A., et al (2006). Tumor imaging using a picomolar affinity HER2 binding affibody molecule. 66, 4339-4348.
Orlova, A., et al (2007). Evaluation of [(111/114m)In]CHX-A"-DTPA-ZHER2:342, an affibody ligand coniugate for targeting of HER2-expressing malignant tumors. Q. J. Nucl. Med. Mol. Imaging 51, 314-323.
Park, B.-W., et al (2000). Rationally designed anti-HER2/neu peptide mimetic disables p185HER2/neu tyrosine kinases in vitro and in vivo. Nat Biotechnol 18, 194-198.
Pils, D., et al (2007). In ovarian cancer the prognostic influence of HER2/neu is not dependent on the CXCR4/SDF-1 signalling pathway. Br. J. Cancer, 96, 485-491.
Ronnmark, J., et al (2002). Human immunoglobulin A (IgA)-specific ligands from combinatorial engineering of protein A. Eur. J. Biochem. 269, 2647-2655.
Ropero, S., et al. "Trastuzumab plus tamoxifen: anti-proliferative and molecular interactions in breast carcinoma." Breast cancer research and treatment 86.2 (2004): 125-137.
Signoretti, S., et al. (2000). Her-2-neu expression and progression toward androgen independence in human prostate cancer. J. Natl. Cancer Inst. 92, 1918-1925.
Subik, K, et al. (2010). The expression patterns of ER, PR, HER2, CK516, EGFR, Ki-67 and AR by immunohistochemical analysis in breast cancer cell lines. Breast cancer: basic and clinical research, 4, 117822341000400004.
Tai, W., et al (2010). The role of HER2 in cancer therapy and targeted drug delivery. J. Control. Release, 146, 264-275.
Tran, T., et al (2007). (99m)Tc-maEEE-Z(HER2:342), an Affibody molecule-based tracer for the detection of HER2 expression in malignant tumors. Bioconjug. Chem. 18, 1956-1964.
Walsh, A. S., et al (2011). DNA cage delivery to mammalian cells. ACS Nano 5, 5427-5432.
Wikman, M., et al (2004). Selection and characterization of HER2/neu-binding affibody ligands. Protein Eng. Des. Sel. 17, 455-462.
Yarden, Y., et al (2001). Untangling the ErbB signaling network. Nat. Rev. Mol. Cell Bio. 2, 127-137.

* cited by examiner

PEPTIDE-DNA CHIMERAS FOR TREATMENT OF HER OVEREXPRESSING CANCERS

CROSS-REFERENCE TO RELATED APPLICATIONS

This application represents the national stage entry of PCT International Application No. PCT/US2017/031548, filed on May 8, 2017, and claims the benefit of U.S. Application Ser. No. 62/338,000, filed on May 18, 2016, which is incorporated by reference herein as if set forth in its entirety.

STATEMENT REGARDING FEDERALLY SPONSORED RESEARCH

Not applicable.

BACKGROUND

Metastasis is the process by which a cancer cell locally invades the surrounding tissue, moves to the microvasculature of the blood and lymph system, migrates into distant tissues, and proliferates into a macroscopic secondary tumor. Cancer cell metastasis may occur at any stage of cancer development with more frequent incidence during last stage of cancers. All current strategies for the treatment of most kinds of cancer focus on removing the primary tumor directly (by surgery) or inhibiting the growth of the cancer (by chemotherapy and radiation). No specific strategy targets metastatic cancer cells. Therefore, the current survival rate for the metastatic cancer patients is extremely low even with optimal combination treatment via surgery, chemotherapy, and radiation. Comparatively, most cancers treated early have a high disease-free survival with optimal combination treatment because of the lower incidence rate of metastasis. For example, for stage 1 breast cancer patients, the 5-year survival rate is close 100%. For stage 2 and 3 patients, the 5-year survival rates are 93% and 72%, respectively. However, for metastatic breast cancer patients (stage 4), the 5 year survival rate is sharply reduced to 16-20%, even with currently optimal combination treatment.

Several kinds of cancer, such as breast, ovarian, gastric, prostate, lung and other cancers are associated with overexpression of human epidermal growth factor receptor 2 (HER2), which is a member of transmembrane receptor family that includes four HER receptors (HER1/EGFR, HER2, HER3 and HER4).[1,2] HER receptors are essential to regulate cell proliferation and differentiation through interlinked signal transduction including Ras/Raf/MEK/MAPK and PI3K/Akt pathways.[3] Ligand binding to the extracellular region induces the heterodimerization of HER receptors and the autophosphorylation of the HER cytoplasmic kinase domains (except for HER3 that has no kinase domain), which leads to the initiation of downstream signaling pathways.[4] Inappropriate activation of HER receptors is associated with the initiation and development of many cancers.

As a key gene in cells, HER2 gene amplification and protein overexpression have been found in breast, ovarian, gastric, prostate, lung and other cancers.[5, 6] The level of HER2 overexpression ranges widely between different cancer cells and different cancer stages. The HER2 overexpression level is much higher in advanced stage of cancers.[7-9] For example, overexpression of HER2 protein or amplification of its gene occurs in 28% of human ovarian cancer cases at all stages of disease;[7] but the rate reaches almost 100% in stage III and IV.[8] Comparably, the overall rate of HER2 overexpression among all prostate cancer cases is 25%, but the overexpression rate in late stage of prostate tumors is 78%.[9] Overexpression of HER2 protein is associated with more frequent recurrence, spread, and significantly poorer prognosis in these kinds of cancer. The greater expression of HER2 in cancer cells than normal tissue and the accessibility of its extracellular domain make HER2 an attractive target to develop strategies for therapeutic intervention. Recently, several monoclonal antibody-based therapeutics, such as trastuzumab (herceptin), pertuzumab, and MM-111, each of which targets the cancer cell surface antigen HER2, have been developed.[4] Subsequently, an antibody-drug conjugate that combines the trastuzumab with a potent microtubule-disrupting agent, DM1 (T-DM1) also has been developed to increase the antibody's efficacy against HER2-positive cancers.[10] However, a significant number of patients either do not respond or quickly relapse and exhibit resistance to existing HER2 therapies.

Small molecule drugs have been attractive agents for cancer treatment for many years because of their small size, oral availability, ability to cross membranes, and low cost. On the other hand, small molecules also have some limitations, such as low specificity and unacceptable toxicity. An antibody-drug conjugate, such as T-DM1 can specifically target to HER2 overexpressed cells. However, every antibody molecule can only delivery a few molecules of a small molecule drug. In addition, the covalent bonds between antibody and drugs limit the release of the small molecule drugs. Accordingly, there remains a need in the art for improved therapeutic compositions and therapeutic strategies for treating late stage, metastatic cancers. In particular, there remains a need for improved therapeutic compositions and methods for treating cancers, including metastatic cancers, associated with overexpression of HER2.

SUMMARY

The present disclosure overcomes the aforementioned drawbacks by providing improved therapeutic compositions and methods for treating cancers associated with overexpression of HER.

In a first aspect, provided herein is a peptide-polynucleotide chimera comprising a HER-binding peptide, a linker, and a single stranded polynucleotide. The HER binding peptide can have a length of about 10 amino acids to about 1000 amino acids. In some cases, a HER2 binding peptide can be an affibody comprising amino acid sequence SEQ ID NO:5. The polynucleotide can be a single-stranded DNA polynucleotide. The single-stranded DNA polynucleotide can have a length of about 10 bases to about 1000 bases. The single-stranded DNA polynucleotide can be selected from the group consisting of SEQ ID NO: 1, SEQID NO:2, SEQ ID NO:3, SEQ ID NO:4, SEQ ID NO:6, SEQ ID NO:7, SEQ ID NO:8, and SEQ ID NO:9.

In another aspect, provided herein are peptide-polynucleotide nanoparticles comprising one or more (e.g., 1-100) peptide-polynucleotide chimeras as described herein. In some cases, the peptide-polynucleotide nanoparticle comprises two peptide-polynucleotide chimeras and two single-stranded DNA polynucleotides. The two single-stranded DNA polynucleotides can be selected from the group consisting of SEQ ID NO: 1, SEQID NO:2, SEQ ID NO:3, SEQ ID NO:4, SEQ ID NO:6, SEQ ID NO:7, SEQ ID NO:8, and SEQ ID NO:9.

In some cases, the peptide-polynucleotide tetrahedron complex further comprises multiple molecules of a small molecule drug covalently or non-covalently bound to the peptide-polynucleotide tetrahedron complex. The small molecule drug can be selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

In another aspect, provided herein is a polynucleotide tetrahedron-affibody-drug complex comprising a DNA tetrahedron having a total of six edges, four affibody molecules, and multiple molecules of a small molecule drug covalently or non-covalently bound to the DNA tetrahedron. The four affibody molecules can be located on four edges of the DNA tetrahedron. The four affibody molecules can be located on four apexes of the DNA tetrahedron. The DNA tetrahedron can comprise four polynucleotides selected from the group consisting of SEQ ID NO:1, SEQ ID NO:2, SEQ ID NO:3, SEQ ID NO:4, SEQ ID NO:6, SEQ ID NO:7, SEQ ID NO:8, and SEQ ID NO:9. The small molecule drug can be selected from the group consisting of doxorubicin, daunorubicin, etoposide, camptothecin, cisplatin, mitomycin C, bleomycin, cyclophosphamide, 5-fluorouracil, hydroxyurea, cytosine arabinoside, and gemcitabine.

In a further aspect, provided herein is a method of treating a cancer associated with overexpression of human epidermal growth factor receptor 2 (HER2). The method can also be used to treat cancers overexpressing other members of the human epidermal growth factor receptor family (e.g., HER1, HER3, and HER4). The method can comprise or consist essentially of administering a therapeutically effective amount of a pharmaceutical composition comprising the peptide-polynucleotide tetrahedron complex as provided herein to a subject in need thereof, whereby administration of the composition treats a cancer associated with overexpression of HER2. The cancer can be selected from the group consisting of breast, ovarian, gastric, prostate, and lung cancer. The cancer can be metastatic cancer. The cancer can be a late-stage cancer. The method of administration can be by injection or by a catheter in communication with a drug delivery pump.

In another aspect, provided herein is a method of suppressing gene expression in target cells of a mammal, comprising the steps of administering a peptide-polynucleotide complex as provided herein, whereby administration of the complex suppresses expression of Her2 in the target cells.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

The cleavage rate constants ($k_{cl}$) were determined by fitting the data to the equation [100−% cleavage]=$100e^{-kt}$.

Figures 11A, 11B, 11C:
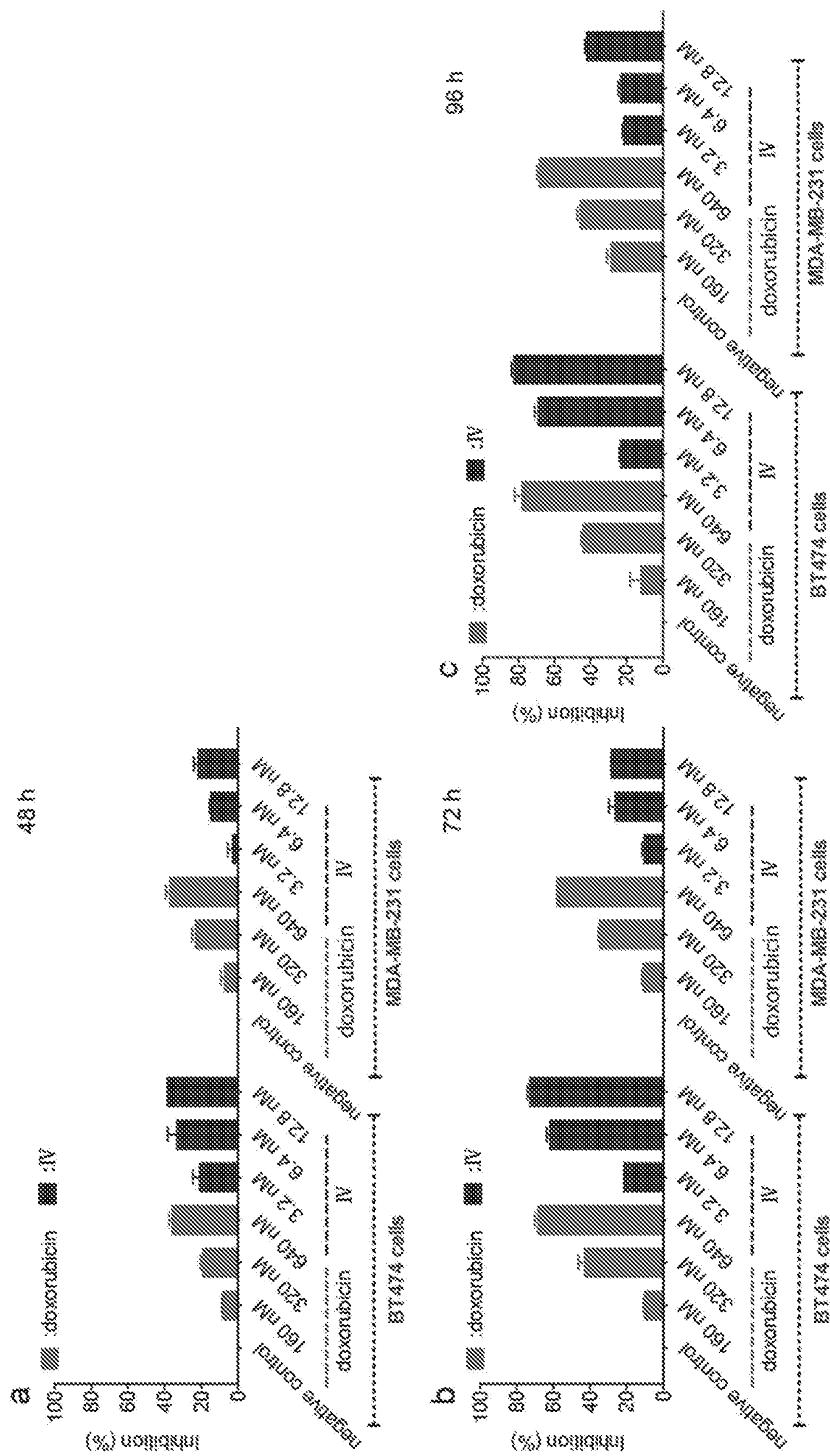

FIGS. 11A-11C demonstrate inhibition of the cell growth of HER2$^+$ BT474 and MDA-MB-231 cancer cells by a DNA tetrahedron-affibody-doxorubicin nanoparticle (IV). The ratio of IV and DOX was 1:50. Cell growth was measured using an MTT assay after (a) 48-hour, (b) 72-hour, or (c) 96-hour treatment with DOX and IV. The data are expressed as a percentage of the control with the means±standard deviation (SD).

Figure 12:
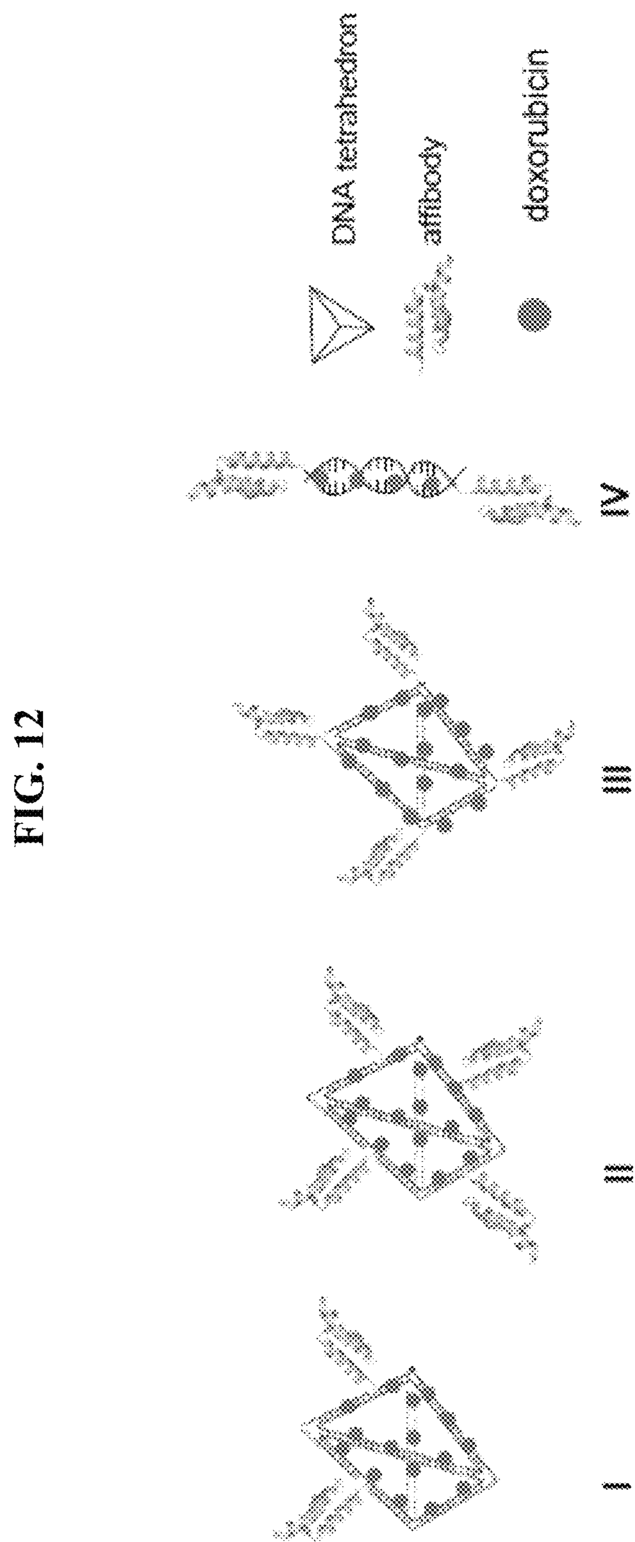

FIG. 12 presents exemplary structures of symmetric and asymmetric DNA-tetrahedron nanoparticles (IV, V, and VI) comprising four affibody molecules on a six-edged DNA tetrahedron; and nanoparticles comprising two affibody or three affibody molecules (VII and VIII).

Figure 13:
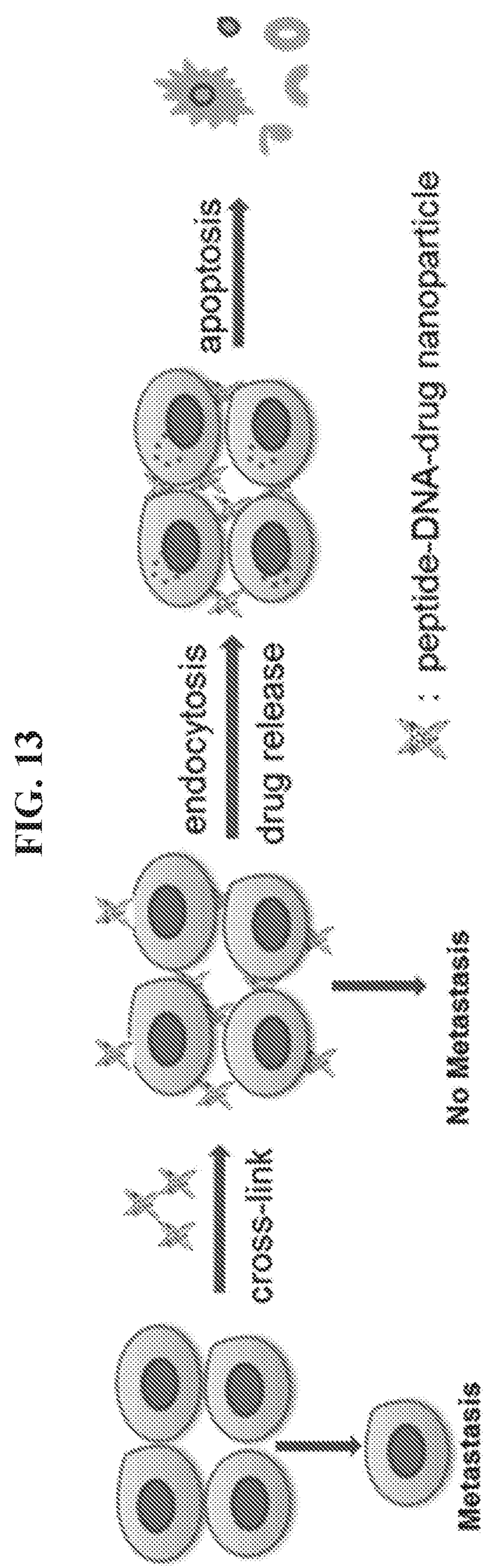

FIG. 13 illustrates an exemplary strategy for blocking metastasis and inducing cancer cell death by administering a peptide-DNA-drug nanoparticle as described herein.

FIGS. 14A-14D present data from an aggregation assay of HER2$^+$ BT474 breast cancer cells.

Figures 15A, 15B:
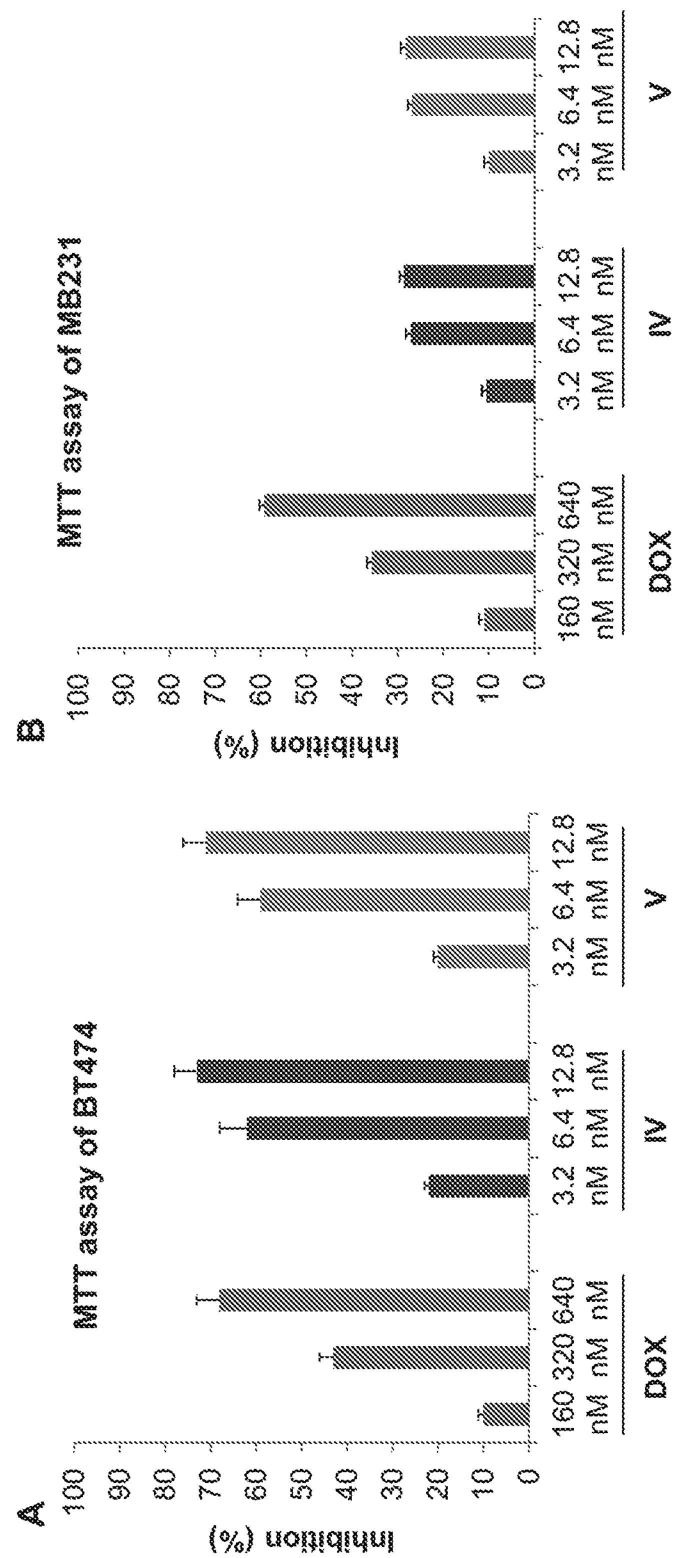

FIGS. 15A-15B present data from an MTT (3-(4,5-dimethylthiazol-2-yl)-2,5-diphenyltetrazolium bromide) assay of HER2$^+$ BT474 cancer cells and HER2$^+$ MDA-MB-231 cancer cells.

FIGS. 16A-16D present data from a migration assay of HER2$^+$ BT474 breast cancer cells.

FIGS. 17A-17D present data from an invasion assay of HER2$^+$ BT474 breast cancer cells.

Figures 18A, 18B:
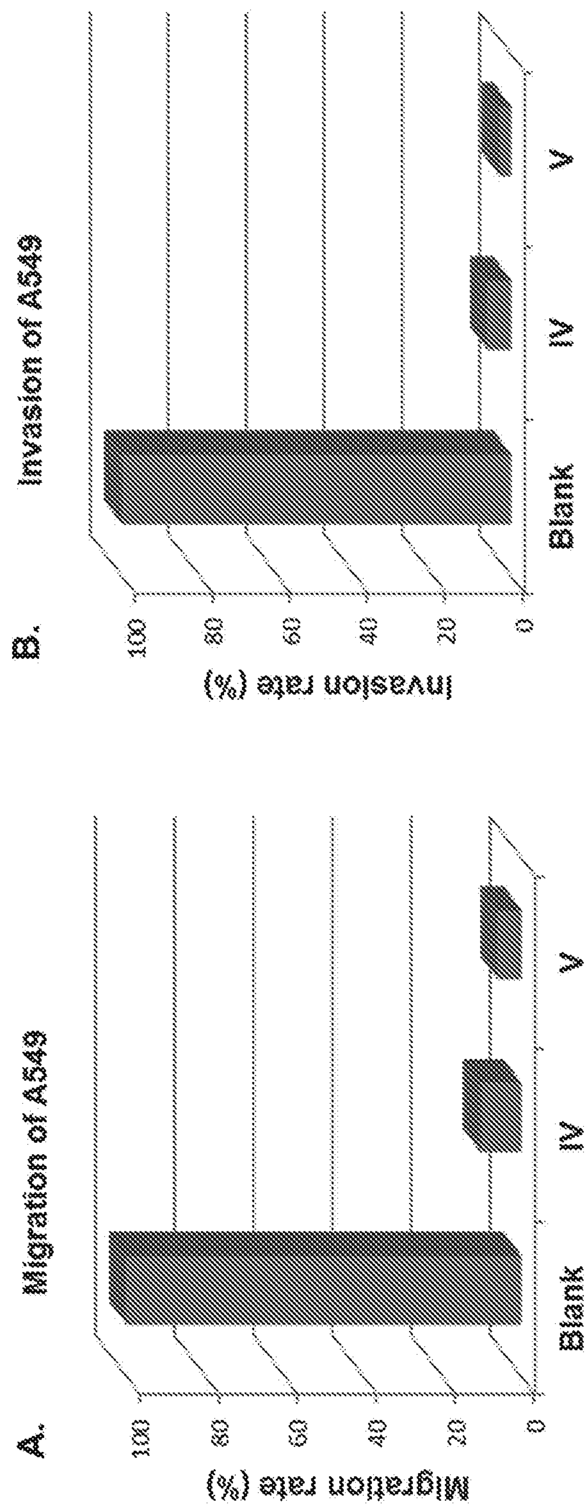

FIGS. 18A-18B present data from migration and invasion assays of lung cancer cell line, A549.

Figures 19A, 19B:
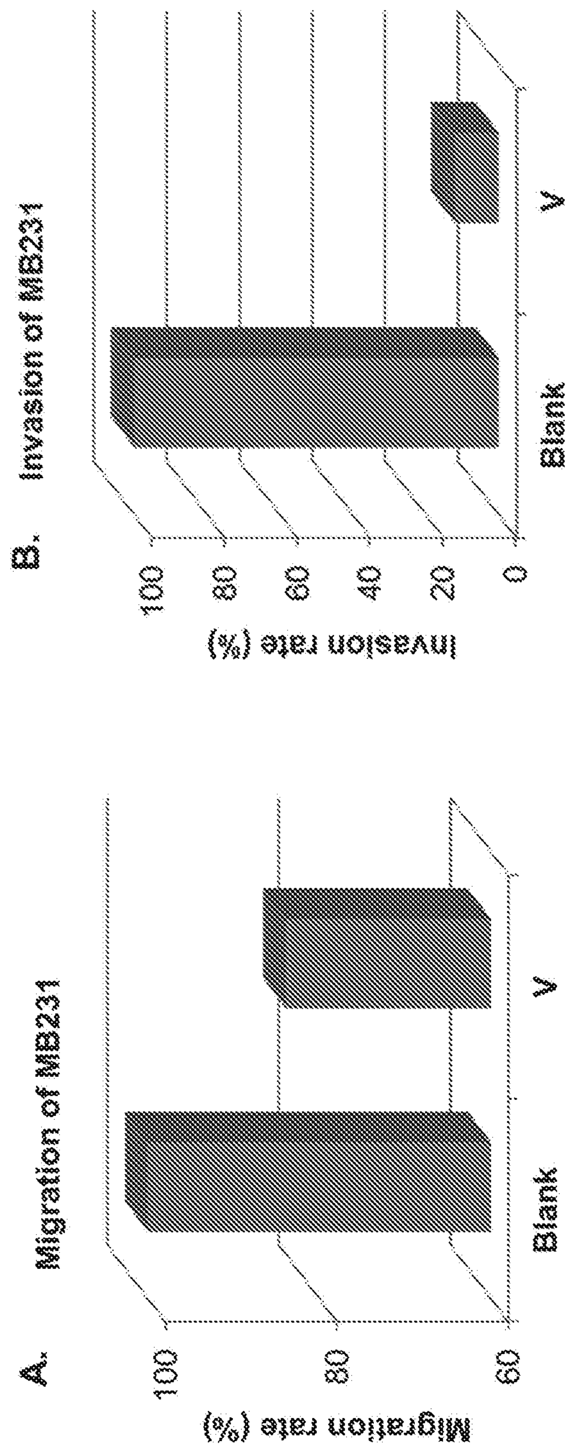

FIGS. 19A-19B present data from migration and invasion assays of breast cancer cell line, MDA-MB-231.

DETAILED DESCRIPTION

Provided herein is a peptide-polynucleotide tetrahedron-drug complex and methods of treating cancers associated with overexpression of genes in the human epidermal growth factor receptor family (e.g., HER1, HER2, HER3, HER4) using compositions comprising such peptide-polynucleotide tetrahedron-drug complexes. The compositions and methods provided herein are based at least in part on the inventors' discovery of a nanostructure complex having inhibitory activity against HER2$^+$ cancer cells. In particular, the inventors demonstrated that the complex specifically targets cancer cells overexpressing HER genes with higher efficiency to inhibit the cancer cells ($IC_{50}$=5.2 nM) and with reduced toxicity to other cells relative to known small molecule drugs.

Figure 1:
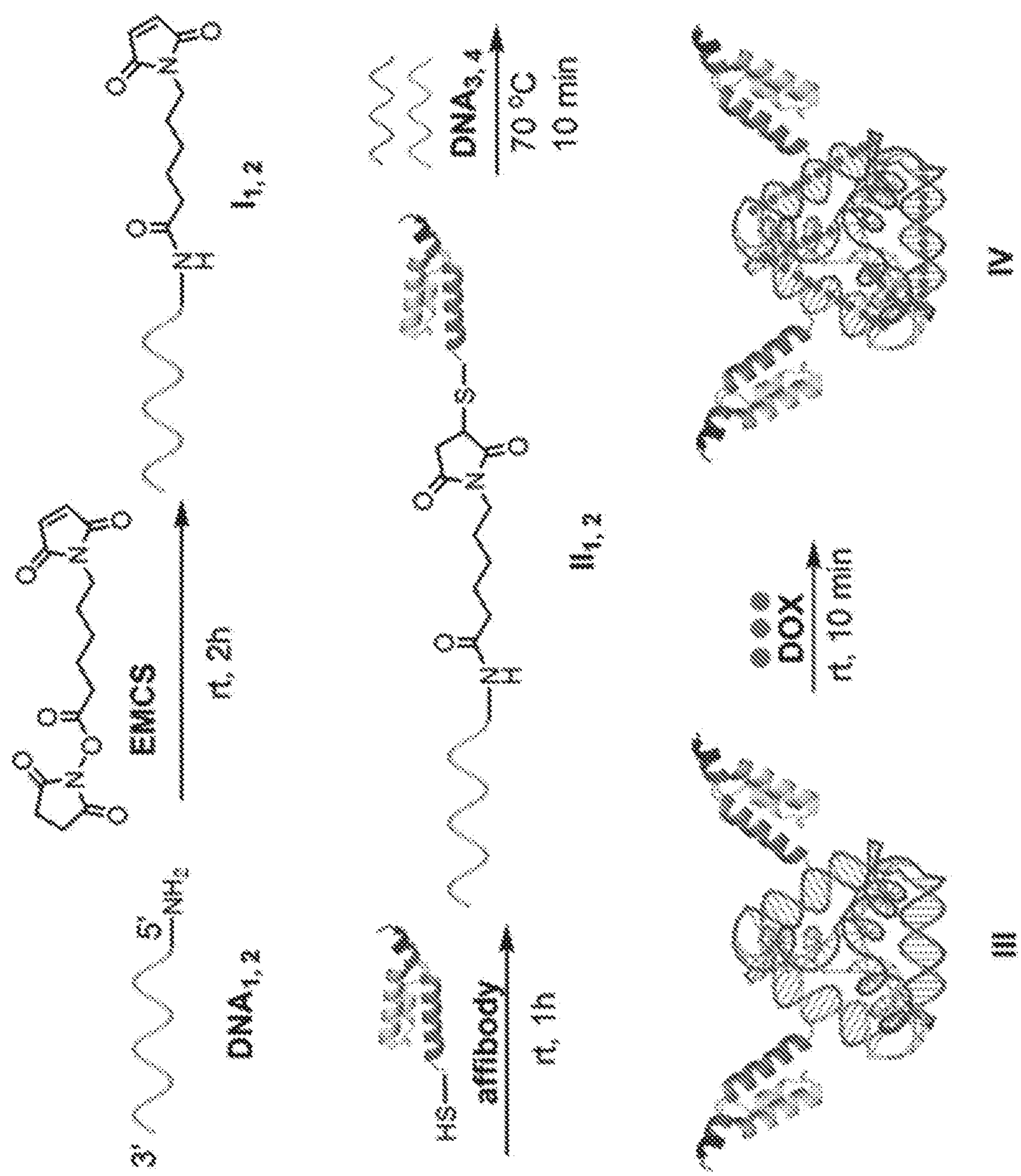
FIG. 1 is an exemplary scheme for preparing a peptide-DNA chimera (also known as a DNA-affibody chimera) (II), a DNA tetrahedron-affibody nanoparticle (III), and DNA-tetrahedron-affibody-drug nanoparticle (IV). EMCS: (N-[ε-maleimidocaproyloxy]succinimide ester); DOX: doxorubicin.

Accordingly, in one aspect, provided herein is a peptide-polynucleotide chimera. Referring to FIG. 1, the peptide-polynucleotide chimera preferably comprises a HER2-binding peptide, a linker, and a single stranded polynucleotide (e.g., a single stranded DNA molecule). As used herein, the term "peptide-polynucleotide chimera" refers to molecules comprising peptide, polypeptide, polynucleotide, or other monomer units.

The terms "peptide," "polypeptide," and "protein" are used interchangeably to refer to a polymer of amino acid residues. The terms apply to amino acid polymers in which one or more amino acid residues is an artificial chemical analog of a corresponding naturally occurring amino acid, as well as to naturally occurring amino acid polymers. The terms polypeptide, peptide, and protein are also inclusive of modifications including, but not limited to, glycosylation, lipid attachment, sulfation, carboxylation, hydroxylation, ADP-ribosylation, and addition of other complex polysaccharides. The terms "residue" or "amino acid residue" or "amino acid" are used interchangeably to refer to an amino acid that is incorporated into a peptide, protein, or polypeptide. The amino acid may be a naturally occurring amino acid and, unless otherwise limited, may encompass non-natural analogues of natural amino acids that can function in a similar manner as naturally occurring amino acids.

The polynucleotide is preferably DNA, RNA, or a DNA or RNA derivative. The length of the polynucleotide can range of 10 to 1000 nucleotides.

In some cases, the peptide or affibody is a polypeptide of the human epidermal growth factor receptor family (e.g., HER1, HER2, HER3, HER4), or a portion thereof. In other cases, the peptide or affibody is a polypeptide that bindings to members of HER family of receptor tyrosine kinases (HER1/EGFR (epidermal growth factor receptor)/c-erbB1, HER2/c-erbB2, HER3/c-erbB3 and HER4/c-erbB4), or a portion thereof. The length of a HER-binding peptide may range from 10 to 1000 amino acids.

The peptide can be a HER2-binding peptide. In some cases, the HER2 binding peptide is an affibody, a short peptide, or a polypeptide/protein. As used herein, the term "affibody" refers to small, highly robust proteins having specific affinities to target proteins. They can be designed and used, for example, like aptamers. Preferably, the affibody molecule has strong affinity for an extracellular domain of HER2 (e.g., an anti-HER2 affibody). In some cases, the HER2 binding peptide is a HER2 affibody comprising three alpha helix bundle domains, the amino acid sequence set forth in SEQ ID NO:5 (MIHHHHHHLQVDNKFNKEMRNAYWEIALLPNLNNQQKRAFIRSLYDDPSQSANLLAEAKKLNDAQAPKVDC), and having a molecular weight of approximately 6 kilodaltons (kDa) and strong affinity for the HER2 receptor (kD 22 pM). Other affibody sequences that can be used include the following: VDNKFNKEMRHAYWEIVKLPNLNPRQKRAFIRSLYDDPSQSANLLAEAKKLNDAQAPKVDC (SEQ ID NO:10) and VDNKFNKELRQAYWEIQALPNLNWTQSRAFIRSLYDDPSQSANLLAEAKKLNDAQAPKVDC (SEQ ID NO: 11). Other suitable affibody sequences are known and available to practitioners in the art.

Suitable linkers for the peptide-polynucleotide chimeras provided herein include, without limitation, crosslinking agents having reactive moieties specific to various functional groups (e.g., sulfhydryls, amines, carbohydrates, azide, and alkyne). Exemplary linkers include, without limitation, N-[ε-maleimidocaproyloxy]succinimide ester; N-[ε-maleimidocaproyloxy]sulfosuccinimide ester; N-(β-Maleimidopropyloxy)succinimide ester; succinimidyl-4-[N-maleimidomethyl]cyclohexane-1-carboxylate; m-maleimidobenzoyl-N-hydroxysuccinimide ester.

Provided herein are peptide-polynucleotide nanoparticles comprising one or more (e.g., 1, 2, 3, 4 . . . 98, 99, 100) peptide-polynucleotide chimeras as described herein. Preferably, two or more peptide-polynucleotide chimeras described herein are associated with each other to form a DNA nanostructure framework. For example, provided herein are peptide-DNA tetrahedron nanoparticles made up of one, two, or more peptide-polynucleotide chimeras as described herein and, in some cases, two polynucleotides. For drug delivery, any DNA structure should be suitable for use. Single-stranded DNA polynucleotides that can be used for the peptide-polynucleotide chimeras and/or the two additional polynucleotides can be selected from the group consisting of: DNA1 (5'-$NH_2$-AGG CAG TTG AGA CGA ACA TTC CTA AGT CTG AAA TTT ATC ACC CGC CAT AGT AGA CGT ATC ACC-3'); $DNA_2$ (5'-$NH_2$-CCT CGC ATG ACT CAA CTG CCT GGT GAT ACG AGG ATG GGC ATG CTC TTC CCG ACG GTA TTG GAC-3' (SEQ ID NO:2)); DNA3 (5'-CTT GCT ACA CGA TTC AGA CTT AGG AAT GTT CGA CAT GCG AGG GTC CAA TAC CGA CGA TTA CAG-3' (SEQ ID NO:3)); and DNA4 (5'-GGT GAT AAAACG TGT AGC AAG CTG TAA TCG ACG GGA AGA GCA TGC CCA TCC ACT ACT ATG GCG-3' (SEQ ID NO:4)). Other polynucleotide sequences suitable for use according to the peptide-DNA tetrahedron nanoparticles described herein include: DNA5 (5'-$NH_2$-CAA CTG CCT AGA CGA ACA TTC CTA AGT CTG AAA TTT ATC ACC CGC CAT AGT AGA CGT ATC ACC-3' (SEQ ID NO:6)); DNA6 (5'-$NH_2$-CCT CGC ATG ACT AGG CAG TTG GGT GAT ACG AGG ATG GGC ATG CTC TTC CCG ACG GTA TTG GAC-3' (SEQ ID NO:7)); DNA7 (5'-TGT AGC AAG CGA TTC AGA CTT AGG AAT GTT CGA CAT GCG AGG GTC CAA TAC CGA CGA TTA CAG-3' (SEQ ID NO:8)); and DNA8 (5'-GGT GAT AAA ACG CTT GCT ACA CTG TAA TCG ACG GGA AGA GCA TGC CCA TCC ACT ACT ATG GCG-3' (SEQ ID NO:9)).

Referring to FIG. 1, an exemplary protocol for synthesizing a peptide-polynucleotide tetrahedron nanoparticle comprises reacting two peptide-polynucleotide chimeras (e.g., affibody-polynucleotide chimeras) and two DNA molecules in the presence of 10 mM Tris-HCl, pH 8.0, containing 10 mM of $MgCl_2$, and incubating the reaction mixture at about 60° C. to about 90° C. Generally, DNA tetrahedron structures are described by Walsh et al., ACS Nano 5:5427-5432 (2011).

Figure 2:
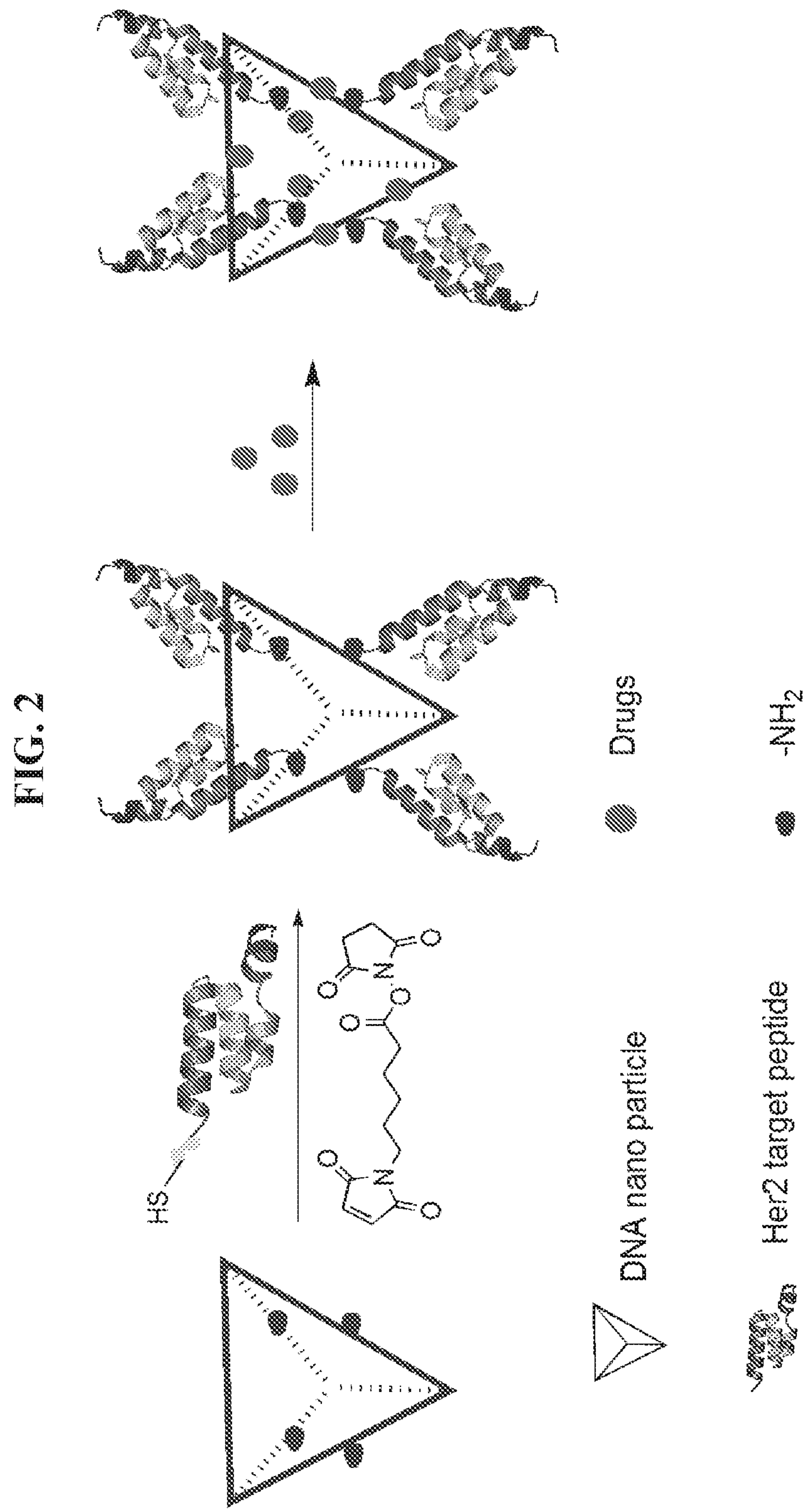
FIG. 2 illustrates an exemplary scheme for preparing a peptide-DNA tetrahedron-drug nanoparticle comprising a HER2 affibody attached to a DNA tetrahedron and a plurality of molecules of a small molecule drug such as an anti-cancer agent.
Figure 3:
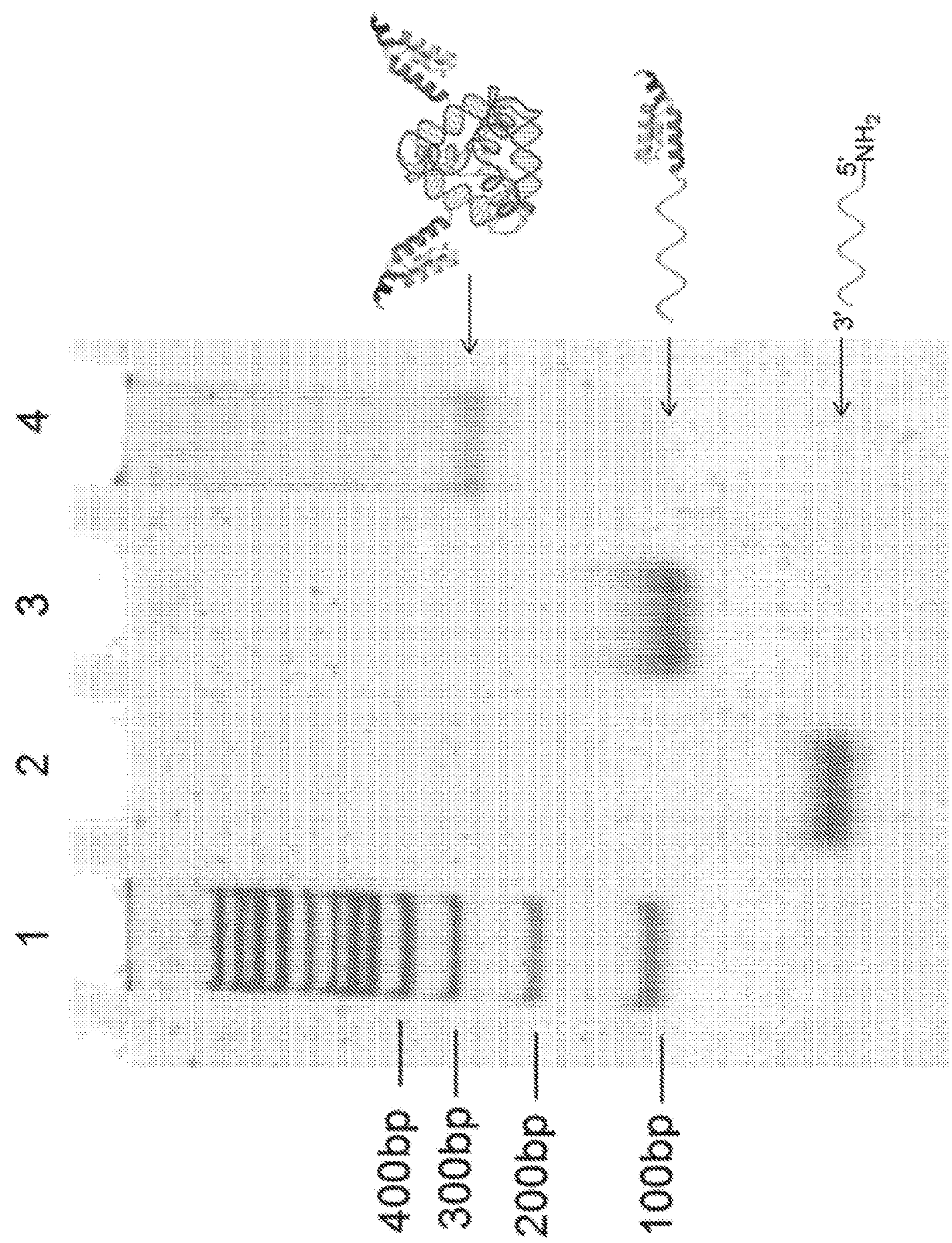
FIG. 3 is an image showing analysis of DNA-affibody chimera (II) and DNA tetrahedron-affibody nanoparticle (III) using native 5% polyacrylamide gel electrophoresis. The gel was run at 110 V for 1 hour, and stained with ethidium bromide. Lane 1, DNA marker (100 bp); lane 2, $DNA_1$ (63 nt); lane 3, $DNA_1$-affibody chimera (II); lane 4, DNA tetrahedron-affibody nanoparticle (III).

In another aspect, provided herein is a peptide-DNA tetrahedron-drug nanoparticle (IV) comprising a peptide-DNA tetrahedron nanoparticle as described herein and a plurality of molecules of a small molecule drug. The plurality of molecules can be bound to the nanoparticle through non-covalent binding or covalent binding. By appending a HER2-binding peptide (e.g., an anti-HER2 affibody) to a tetrahedral DNA nanostructure, one may obtain a functional, multiform DNA nanostructure useful for as carriers for delivery of drugs or other compounds or biomolecules. For example, peptide polynucleotide tetrahedron nanostructures provide a high capacity vehicle for binding and delivering small molecule anti-cancer drugs to target cells. The peptide-polynucleotide tetrahedron-drug complex as shown in FIGS. 1, 2, and 12 demonstrates greater binding capacity for HER2 overexpressed cancer cells as compared to small molecule drugs not associated with such a nanostructure. In addition, the peptide-polynucleotide tetrahedron-drug complex shows greater efficacy for inhibiting HER2 overexpressed cancer cells as well as decrease toxicity for normal cells. Accordingly, the peptide-polynucleotide tetrahedron-drug complexes described herein provide a novel class of anti-cancer drugs.

Small molecule drugs for inclusion in a peptide-polynucleotide tetrahedron-drug complex described herein include, without limitation, doxorubicin (DOX), daunorubicin, etoposide, camptothecin, cisplatin, mitomycin C, bleomycin, cyclophosphamide, 5-fluorouracil, hydroxyurea, cytosine arabinoside, and gemcitabine. For example, DOX is a broad spectrum, FDA-approved drug anticancer agent that binds reversibly to DNA. The target of the peptide-tetrahedron-drug nanoparticle (III) includes all HER2 positive cancer cells including, without limitation, breast, ovarian, gastric, prostate, lung, and other cancers.

Referring to FIG. 2, the peptide-polynucleotide chimeras and peptide-polynucleotide tetrahedron-drug nanoparticles described herein provide a highly efficient approach to specifically delivering small molecule drugs to HER2 overexpressed cancer cells. When a plurality of molecules of a small molecule drug are bound to a nanoparticle as described herein via non-covalent binding, the plurality of molecules can dissociate from the nanoparticle upon entry or contact to the target cancer cell. Each vehicle nanostructure has capacity to delivery tens to hundreds of molecules of an anti-cancer drug. Without being bound by any particular theory or mode of action, it is believed that an anti-HER2 peptide or affibody attached to a DNA tetrahedron will also bind a small molecule anticancer agent such as doxorubicin to target and bind HER2 expressing cancer cells and, consequently, block metastasis and induce apoptosis of targeted HER2+ cancer cells.

In some cases, it may be advantageous to attach one or more of the above-identified small molecule drugs to the peptide-DNA tetrahedron using, for example, a degradable linker. Linkers suitable for the nanoparticles described herein include, without limitation, DNA, RNA, peptides, polysaccharides, esters, amides, and disulfide bonds.

In another aspect, provided herein is a polynucleotide tetrahedron-affibody-drug complex, where the complex comprises a DNA tetrahedron having a total of six edges, four affibody molecules, and multiple molecules of a small molecule drug covalently or non-covalently bound to the DNA tetrahedron. Referring to FIG. 12, the four affibody molecules can be located on four edges of the DNA tetrahedron, forming an asymmetric structure. Alternatively, the four affibody molecules can be located on four apexes of the DNA tetrahedron, forming a symmetric structure. DNA tetrahedron can comprise four DNA polynucleotides, which can be selected from the group consisting of SEQ ID NO: 1, SEQ ID NO:2, SEQ ID NO:3, SEQ ID NO:4, SEQ ID NO:6, SEQ ID NO:7, SEQ ID NO:8, and SEQ ID NO:9. In certain embodiments, the nanoparticles can be other structures, such as linear type, Y-type, or polygon structures, or any other geometric structure recognized as suitable by persons of ordinary skill in the art in view of the teachings herein. As shown in FIG. 12, the small molecule drug can be doxorubicin. Other small molecule drugs include, without limitation, daunorubicin, etoposide, camptothecin, cisplatin, mitomycin C, bleomycin, cyclophosphamide, 5-fluorouracil, hydroxyurea, cytosine arabinoside, gemcitabine, and the like.

In a further aspect, provided herein are methods for treating cancers associated with overexpression of HER2 or other HER molecules. As used herein, the terms "treating," "treat," and "treatment" refer to the management and care of a patient for the purpose of combating the disease, condition, or disorder. The terms embrace both preventative, i.e., prophylactic, and palliative treatments. In some cases, the term "treated" refers to any beneficial effect on progression of a disease or condition. Beneficial effects can include reversing, alleviating, inhibiting the progress of, preventing, or reducing the likelihood of the disease or condition to which the term applies or one or more symptoms or manifestations of such a disease or condition. Where the disease or condition is a tumor, cancer, or cancer-associated condition, treating can refer to the management and care of a patient for the purpose of combating cancer, and can include reversing, alleviating, inhibiting the progress of, preventing, reducing the size of, or reducing the likelihood of, or lessening the severity of any aspect of the cancer or cancer-associated condition (e.g., metastasis, tumor growth). A therapeutic beneficial effect on the health and well-being of a patient includes, but it not limited to: (1) curing the cancer; (2) slowing the progress of the cancer; (3) causing the tumor to regress; or (4) alleviating one or more symptoms of the cancer. As used herein, the terms "preventing" and "prevent" refer not only to a complete prevention of a certain disease or condition, but also to partially or substantially attenuating, reducing the risk of, or delaying the development or recurrence of the disease or condition to which the term applies.

In some cases the methods provided herein are directed to treating or preventing a tumor cancer in a subject by administering a therapeutically effective amount of a compound provided herein. A "therapeutically effective amount" of a compound refers to an amount of the compound that alleviates, in whole or in part, symptoms associated with a disorder or disease, or slows or halts further progression or worsening of those symptoms, or prevents or provides prophylaxis for the disease or disorder in a subject at risk for developing the disease or disorder. A therapeutically effective dose relates to the amount of a compound which is sufficient to improve the symptoms, for example a treatment, healing, prevention or improvement of such conditions. In exemplary embodiments, a therapeutically effective amount or dose is an amount such that free antibody is present in the blood. For dosage determinations, it can be advantageous to assess toxicity and therapeutic efficacy of a compound in cell cultures or in experimental animals. For example, the $LD_{50}$ (i.e., the dose lethal to 50% of the population) and $ED_{50}$ (i.e., the dose therapeutically effective in 50% of the population) can be determined. From these calculations, dosage ranges for use in humans can be formulated. Dosage ranges can vary depending on factors such as mode of administration. A therapeutically effective amount of a pharmaceutical composition provided herein can range from about 0.001 to 100 mg of nanoparticle per kg body weight of the subject (e.g., about 0.01 to 100 mg/kg body weight; about 0.1 to 40 mg/kg body weight; about 1 to 20 mg/kg body weight).

A "subject" or "patient" is a member of any animal species, preferably a mammalian species, optionally a human. The subject can be an apparently healthy individual, an individual suffering from a disease, or an individual being treated for a disease.

The terms "delivering," "deliver," "administering," and "administers" can be used interchangeably to indicate the introduction of any agent (e.g., a therapeutic agent) into the body of a patient in need thereof to treat a disease or condition, and can further mean the introduction of any agent into the body for any purpose. The terms encompass any route of introducing or delivering to a subject a compound to perform its intended function. A composition comprising a peptide-tetrahedron-drug nanoparticle as provided herein can be delivered or administered to a subject by any method that achieves the intended purpose or is deemed appropriate by those of skill in the art. For example, a composition of the present invention can be administered as a pharmaceutical, and may be administered systemically or locally via oral or parenteral administration. As used herein, the term "administration" includes oral and parenteral administration. Oral administration includes, for example, administration of oral agents. Such oral agents include, for example, granules, powders, tablets, capsules, solutions, emulsions, and suspensions. Parenteral administration includes, for example, administration of injections. Such injections include, for example, subcutaneous injections, intramuscular injections, and intraperitoneal injection. In some cases, intravenous injections such as drip infusions, intramuscular injections, intraperitoneal injections, subcutaneous injections, suppositories, enemas, oral enteric tablets, or the like can be selected. In some cases, the method of administration is by injection or by a catheter in communication with a drug delivery device. "Drug delivery device" encompasses any and all devices that administers a therapeutic agent to a patient and includes infusion pumps, implanted or percutaneous vascular access ports, direct delivery catheter systems, local drug-release devices or any other type of medical device that can be adapted to deliver a therapeutic to a patient.

Appropriate modes of administration can be determined based on the physical location of a tumor or tumors in the subject's body. In exemplary embodiments, a composition comprising a peptide-tetrahedron-drug nanoparticle as provided herein is administered to a subject having a diagnosis of lung cancer or a pre-cancerous lesion, where the composition is administered orally or intravenously. Alternatively, a composition comprising a peptide-tetrahedron-drug nanoparticle can be administered locally to an intended area of treatment. For example, a composition comprising a peptide-tetrahedron-drug nanoparticle can be administered by local injection during surgery.

Compositions can be administered to a subject in need thereof in dosage unit form where each discrete dosage unit contains a predetermined quantity of an active ingredient or compound that was calculated to elicit a desirable therapeutic effect when administered with, in some cases, a pharmaceutically acceptable buffer or carrier. The terms "pharmaceutically acceptable buffer" and "pharmaceutically acceptable carrier" are meant to encompass any buffer or carrier, which does not interfere with the effectiveness of the biological activity of the active ingredient and that is not toxic to the host to which it is administered.

Treatment or prevention according to a method provided herein can occur before, during, or after the subject is treated by surgery, radiation, and/or chemotherapy. In some cases, treatment according to a method provided herein prior to chemo- or radiotherapy may improve the outcome of the conventional therapy. In an exemplary embodiment, a compound as provided herein is administered to a subject concurrently with one or more other treatments or preventative measures such as radiotherapy, chemotherapy, or surgery.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Materials and Methods

Preparing Affibody-Tetrahedron Nanoparticle:

The sequences of four single-strand DNAs are as follows:

```
DNA1:
                                          (SEQ ID NO: 1)
5'-NH2-AGG CAG TTG AGA CGA ACA TTC CTA AGT CTG
AAA TTT ATC ACC CGC CAT AGT AGA CGT ATC ACC-3'

DNA2:
                                          (SEQ ID NO: 2)
5'-NH2-CCT CGC ATG ACT CAA CTG CCT GGT GAT ACG
AGG ATG GGC ATG CTC TTC CCG ACG GTA TTG GAC-3'

DNA3:
                                          (SEQ ID NO: 3)
5'-CTT GCT ACA CGA TTC AGA CTT AGG AAT GTT CGA
CAT GCG AGG GTC CAA TAC CGA CGA TTA CAG-3'

DNA4:
                                          (SEQ ID NO: 4)
5'-GGT GAT AAAACG TGT AGC AAG CTG TAA TCG ACG
GGA AGA GCA TGC CCA TCC ACT ACT ATG GCG-3'
```

The sequence of the affibody used in this study is MIHHHHHHLQVDNKFNKEMRNAYWEIALLPNLNNQQKRAFIRSLYDDPSQSANLLAEAKKLNDAQAPKVDC (SEQ ID NO:5).

The DNAs were purchased from TaKaRa Biotechnology Co., Ltd. (Dalian, China). The affibody was expressed in *E. coli* cells and purified with a Ni-NTA column.

$DNA_1$ or $DNA_2$ (200 μg, 10.3 nmol) was dissolved in 160 μL of phosphate-buffered saline (PBS, 10 mM $PO_4^{3-}$, 137 mM NaCl, and 2.7 mM KCl) and combined with 40 μL of 10 mM N-ε-malemidocaproyl-oxysuccinimide ester (EMCS) in dimethyl sulfoxide. The reaction mixture was incubated at room temperature for 3 hours and quenched by adding 20 μL of 3 M NaOAc. After the addition of 600 μL of ethanol and incubation at 4° C. for 30 minutes, the reaction mixture was centrifuged at 15000 g for 30 minutes. After washing with 70% ethanol, the DNA was dissolved in 50 μL of PBS buffer and affibody (300 μg, 38.1 nmol) in 300 μL of PBS buffer was added. After incubation at room temperature for 2 hours, the reaction mixture was purified on a DEAE-Sepharose column. The column was eluted with PBS buffer containing 0.1~0.6 M NaCl. The purified affibody-DNA chimera was analyzed by 8% denature polyacrylamide gel electrophoresis (PAGE). The gel was run at 110 V for 1 hour, and stained with ethidium bromide.

Figure 4:
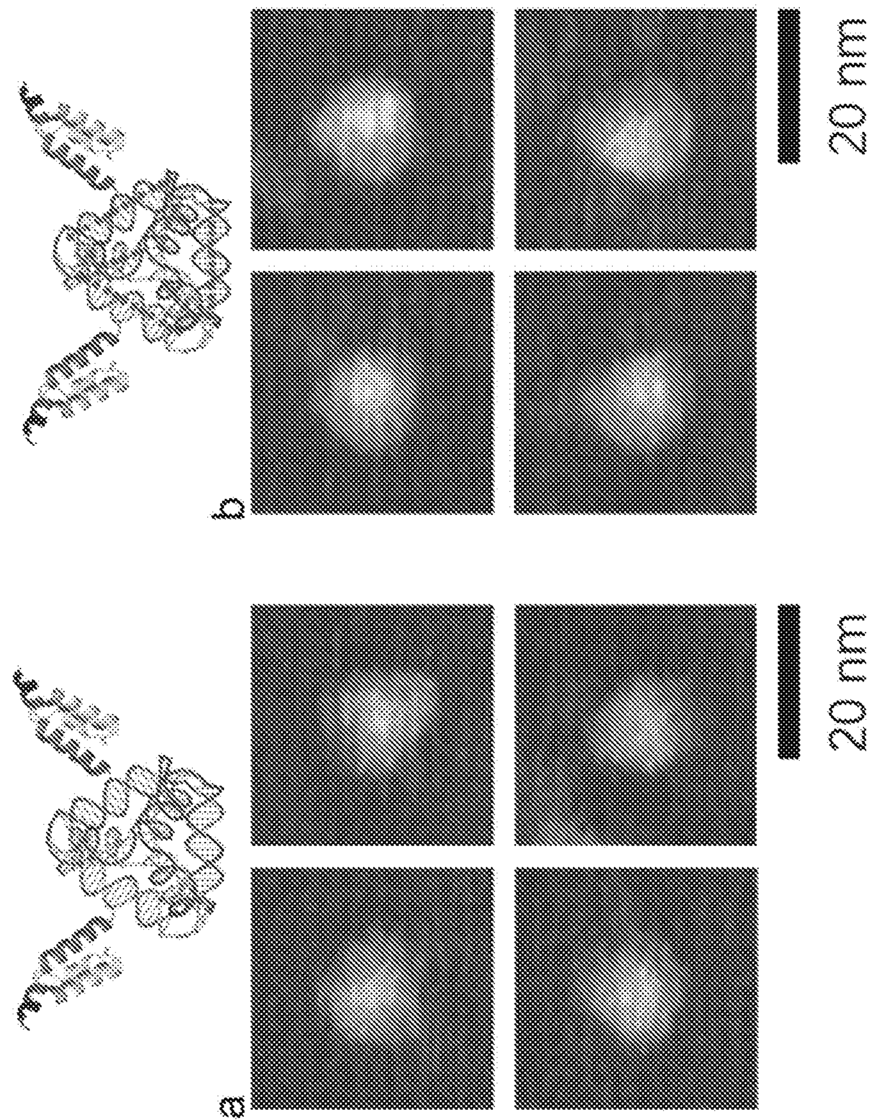
FIGS. 4A-4B are atomic-force microscopy (AFM) micrographs of nanoparticles. (a) Structure of a DNA tetrahedron-affibody nanoparticle (III). (b) Structure of a DNA tetrahedron-affibody-DOX nanoparticle (IV). Scale bars are 20 nm.

Preparation of DNA Tetrahedron-Affibody Nanoparticle[11, 12]:

Affibody-$DNA_1$ (10.0 nmol), affibody-$DNA_2$ (10.0 nmol), $DNA_3$ (10.0 nmol), and $DNA_4$ (10.0 nmol) were added into 8 mL of 10 mM Tris.HCl, pH 8.0, containing 10 mM of $MgCl_2$. The reaction mixture was incubated at 80° C. for 10 minutes, then cooled to room temperature over a period of 30 minutes. The resulting affibody-DNA tetrahedron nanoparticle (93.1 kDa) was analyzed by 5% native polyacrylamide gel electrophoresis (PAGE) (FIG. 4). The gel was run at 110 V for 1 hour, and stained with ethidium bromide.

Preparation of DNA Tetrahedron-Affibody-Doxorubicin Nanoparticle:

The affibody-DNA tetrahedron nanoparticle prepared in the previous step was concentrated using an Amicon® ultra centrifugal filters (MW cut off 50 kDa). The concentrated affibody-DNA tetrahedron nanoparticle (5 μM) in 100 μL of 10 mM Tris.HCl, pH 8.0, containing 12 mM $MgCl_2$ was treated with 5 μL of 10 mM doxorubicin (DOX) and the reaction mixture was incubated at room temperature for 10 minutes. The reaction mixture was purified by removing excess DOX on a Sephadex G-25 column. The concentration of the affibody-DNA tetrahedron-doxorubicin nanoparticle was determined by UV absorption.

Atomic Force Microscopy (AFM) Characterization:

For DNA tetrahedron-affibody nanoparticle imaging, 10-μL samples (10 nM) were deposited onto a freshly peeled mica surface for 2 minutes. Next, 10 μL of 100 mM $NiCl_2$ solution was added to assist adsorption. Finally, 55 μL of TAE/$Mg^{2+}$ buffer (40 mM Tris, 20 mM acetic acid, 2 mM EDTA, 12 mM $MgCl_2$, pH 8.0) was added onto the mica and another 55 μL of TAE/$Mg^{2+}$ buffer was added on the atomic force microscope (AFM) tip. The samples were imaged in ScanAsyst in Fluid mode (with a ScanAsyst-liquid+tip) with Dimension FastScan AFM (Bruker).

Quantification of the DOX/DNA Ratio in the DNA Tetrahedron-DOX Nanoparticle:

The UV absorption of the DNA tetrahedron (0.5 μM) was measured in the range 220-600 nm in a solution of 10 mM Tris-HCl, pH 8.0, containing 12 mM $MgCl_2$. Then different amounts of DOX (5-30 μM) were added to the solution, and the UV absorption was measured. Finally, excess DOX was removed using a Sephadex G-25 column, and the purified DNA tetrahedron-DOX nanoparticle was measured. A standard curve between the $A_{505}/A_{260}$ (Y axis) and the ratio of DOX/tetrahedron (X axis) was prepared. The amount of DOX binding to the DNA tetrahedron in the detection sample was calculated using the equation $y=0.0026x+0.0082$.

Release Assay of Doxorubicin:

Three samples in 1 mL volume were prepared as follows: sample 1, 300 μM DOX in 10 mM Tris-HCl, pH 8.0, containing 12 mM $MgCl_2$; sample 2, 6 μM DNA tetrahedron-affibody-DOX (containing 300 μM DOX) in 10 mM Tris-HCl, pH 8.0, containing 12 mM $MgCl_2$; sample 3, 6 μM DNA tetrahedron-affibody-DOX (containing 300 μM DOX) and 600 units of DNase I in 10 mM Tris-HCl, pH 8.0, containing 12 mM $MgCl_2$ and 1 mM $CaCl_2$. Each sample was transferred into a dialysis tube (1 mL, MW cutoff 10 kDa), which was floated in 100 mL 1× phosphate-buffered saline (PBS, pH 7.4) and continuously stirred at room temperature. At the determined times, 100 μL of PBS buffer was taken out and the fluorescent intensity was measured. The fluorescence spectra of DOX were measured using a Varian Cary Eclipse Fluorescence Spectrophotometer with the excitation slit as 10 nm and emission slit as 10 nm. The samples were excited at 490 nm, and the emission spectra were recorded at the range of 510-700 nm.

DNA Stability Assay in Fetal Bovine Serum:

Three samples in 100 μL of 10 mM Tris-HCl, pH 8.0, containing 12 mM $MgCl_2$ were prepared as follows: sample 1, 24 μM single strand $DNA_1$; sample 2, 6 μM DNA tetrahedron-affibody; sample 3, 6 μM DNA tetrahedron-affibody-DOX (containing 300 μM DOX). Each sample was added into 100 μL of fetal bovine serum and incubated at 37° C. At the determined times, 5 μL of reaction mixture was taken out and added into 5 μL of loading buffer (formamide containing 100 mM EDTA, 80° C.). The reaction mixture was analyzed by 15% denaturing polyacrylamide gel (7 M urea). After electrophoresis in 89 mM Tris buffer, pH 8.0, containing 89 mM boric acid and 2 mM EDTA at 100 V for 1 hour, the gel was stained with ethidium bromide for 30 min and visualized using UV light. The extent of reaction (expressed as the percentage of DNA cleavage) was quantified by utilizing ImageQuant version 5.2 software. The cleavage rate constants ($k_{cl}$) were determined by fitting the data to the equation [100−% cleavage]=$100e^{-kt}$.

Cancer Cell Inhibition Assay:

BT474 human breast cancer cells (ATCC® HTB-20™, overexpression of HER2) and MDA-MB-231 human breast cancer cells (ATCC® HTB-26™, low expression of HER2 receptor) were cultured at 37° C. in a 5% $CO_2$ atmosphere and grown in Gibco® RPMI 1640 medium supplemented with 10% fetal bovine serum (FBS) and 1% antibiotic-antimycotic mix antibiotic supplement before use.

Exponentially growing BT474 cells and MDA-MB-231 cells were harvested and plated in 96-well plates at a concentration of $2\times10^4$ cells/well for BT474 cells and $5\times10^4$ cells/well for MDA-MB231 cells. After incubation at 37° C. for 24 hours, the cells were treated with trastuzumab, DNA tetrahedron-affibody III and DNA tetrahedron-affibody-doxorubicin nanoparticle IV (1:50 III-doxorubicin) at different concentrations for an additional 48, 72, or 96 hours. Then 20 μL of MTT (5 mg/mL) was added to each well and the plates were incubated at 37° C. for 4 hours. The supernatant was discarded, and 100 μL of DMSO was added to each well. The absorbance was recorded at 490 nm after 15 minutes. Inhibition of cell growth was obtained by the following formula:

$$\text{Inhibition }(\%)=(OD_{Treatment}-OD_{background})/(OD_{Nagative\ control}-OD_{background})\times100\%$$

Data are reported as the mean of three independent experiments, each run in quintuplicate.

HER2 Binding Assay of BT474 and MDA-MB-231 Cells:

BT474 cells and MDA-MB-231 cells were grown on glass bottom microwell disks at a cell density of approximately 10,000 cells/well at 37° C. for 48 hours. When the cell confluency reached about 70%, the cells were treated with doxorubicin and DNA tetrahedron-affibody-doxorubicin nanoparticle IV (1:50 III-doxorubicin) at 1 μM concentration for 1 hour. Then the cells were stained using 2.5 μg/mL DAPI (Invitrogen) for 30 minutes after the cells were rinsed with phosphate buffered saline (PBS) for two times. Finally, the cells were fixed with 4% paraformaldehyde for 10 minutes. The fluorescent images were obtained using a fluorescence microscope (Nikon Ti-U, Japan) with red and green filters. Thereafter, all images were recorded and the target cells counted using a 40× oil objective. To ensure accurate intensity measurements, the exposure time (3000 ms) and laser time were kept the same. The mean pixel intensity within the region of interest was calculated. Data are reported as the mean of three independent experiments, each run in quintuplicate. The data was expressed as mean±SD.

Migration Assay.

The 24-well transwell chambers (8 μm pore size) were balanced with 200 μL of RPMI 1640 medium (serum free) for 2 h at 37° C. in 5% $CO_2$ atmosphere. After removing the medium, $3.6\times10^4$ cells in 180 μL of RPMI 1640 medium (serum free) were added to each chamber followed by adding 20 μL of nanoparticles (200 nM) or 20 μL Tris-HCl (10 mM, pH 8.0). To the lower compartment of each well was added 800 μL of RPMI 1640 medium containing 10% serum. After incubation for 48 hours, cells were fixed with 4% formaldehyde followed by 100% methanol and stained with 0.2% crystal violet. The non-migrated cells on the upper surface of the chamber were removed with a cotton swab and the migrated cells on the lower surface of the chamber were imaged under a light microscope.

Invasion Assay.

The 24-well transwell chambers (8 μm pore size) were coated with 100 μL of Matrigel® matrix (150 mg/mL) for 2 h at 37° C. in 5% $CO_2$ atmosphere. After removing the uncoated solution, $3.6\times10^4$ cells in 180 μL of RPMI 1640 medium (serum free) were added to each chamber followed by adding 20 μL of nanoparticles (200 nM) or 20 μL Tris-HCl (10 mM, pH 8.0). To the lower compartment of each well was added 800 μL of RPMI 1640 medium containing 10% serum. After incubation for 48 hours, cells were fixed with 4% formaldehyde followed by 100% methanol and stained with 0.2% crystal violet. The non-migrated cells on the upper surface of the chamber were removed with a cotton swab and the migrated cells on the lower surface of the chamber were imaged under a light microscope.

Figure 5:
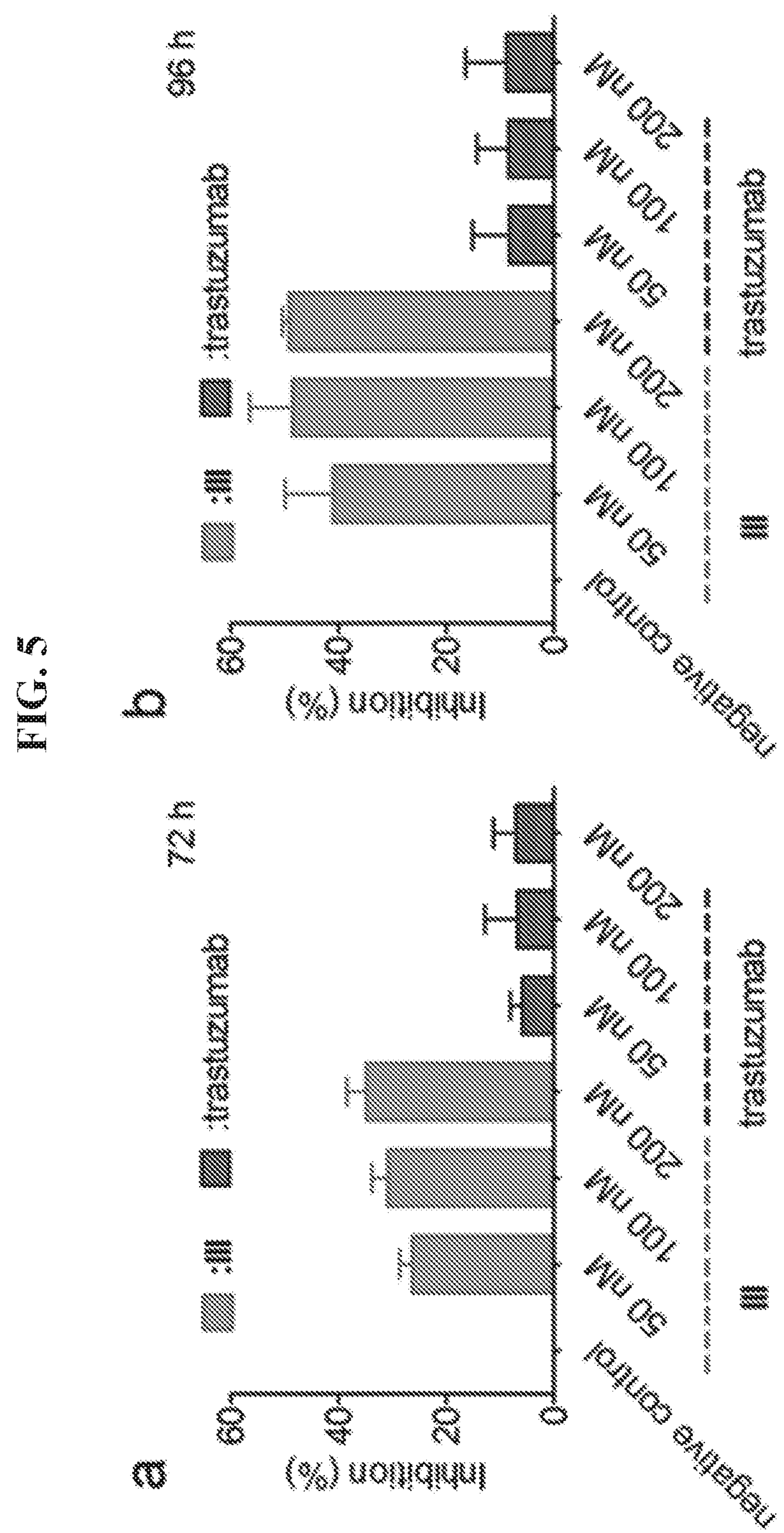
FIGS. 5A-5B demonstrate inhibition of BT474 cell growth by DNA tetrahedron-affibody nanoparticle (III). Cell growth was measured using an MTT assay after (a) 72 hours or (b) 96 hours treatment with the DNA tetrahedron-affibody nanoparticle (III) and trastuzmab. The results are expressed as a percentage of the control with the means±standard deviation.

Results:

This Example sets forth a method to prepare a DNA-affibody nanoparticle containing one DNA tetrahedron and two affibody molecules to mimic one Fc and two Fab regions of the antibody structure. In addition to functioning as a scaffold to anchor two affibody molecules, the DNA tetrahedron also was used as a vehicle to non-covalently bind multiple copies of a small molecule drug for specific drug delivery. As shown in FIG. 1, two 5'-$NH_2$ labeled DNAs ($DNA_{1,2}$) were treated with $N^{\varepsilon}$-malemidocaproyloxysuccinimide ester (EMCS) to generate two $N^{\varepsilon}$-malemidocaproyloxy-DNAs ($I_{1,2}$).[13] The DNAs so obtained were treated with an affibody, which contained a cysteine residue at the C-terminus afford DNA-affibody chimeras ($II_{1,2}$). The affibody containing a hexahistidine tag at its N-terminus was expressed in *E. coli* BL21 cells and purified using a Ni-NTA column (data not shown).[14-16] The coupling reaction yields between $I_{1,2}$ and the affibody did not differ when the incubation times ranged from 1 to 5 hours (data not shown. The generated DNA-affibody chimeras were then purified using a DEAE-Sepharose CL-6B column to remove the excess affibody in the reaction mixture following a published procedure for purification of oligonucleotides (data not shown).[17] The unreacted DNAs in the eluate after DEAE-Sepharose CL-6B chromatography were removed by Ni-NTA chromatography, which specifically binds the hexahistidine peptide attached to the affibody (data not shown). After purification, the DNA-affibody chimeras were characterized by treatment with ethidium bromide and Coomassie Brilliant Blue R-250, which stained the DNA and protein, respectively (data not shown). Then, the two pure DNA-affibody chimeras ($II_{1,2}$) were combined with two single-strand DNAs ($DNA_3$ and $DNA_4$) to form an affibody-tetrahedron structure (III),[12] which contained two affibody molecules and one DNA tetrahedron particle. This structure was characterized by 5% native polyacrylamide gel electrophoresis (FIG. 4) and by using atomic force microscopy (AFM) (FIG. 5A). Since only one face of the tetrahedron attached to the mica surface, the top view of the nanoparticle III by AFM was a triangle exhibiting a brighter apex.

Figure 6:
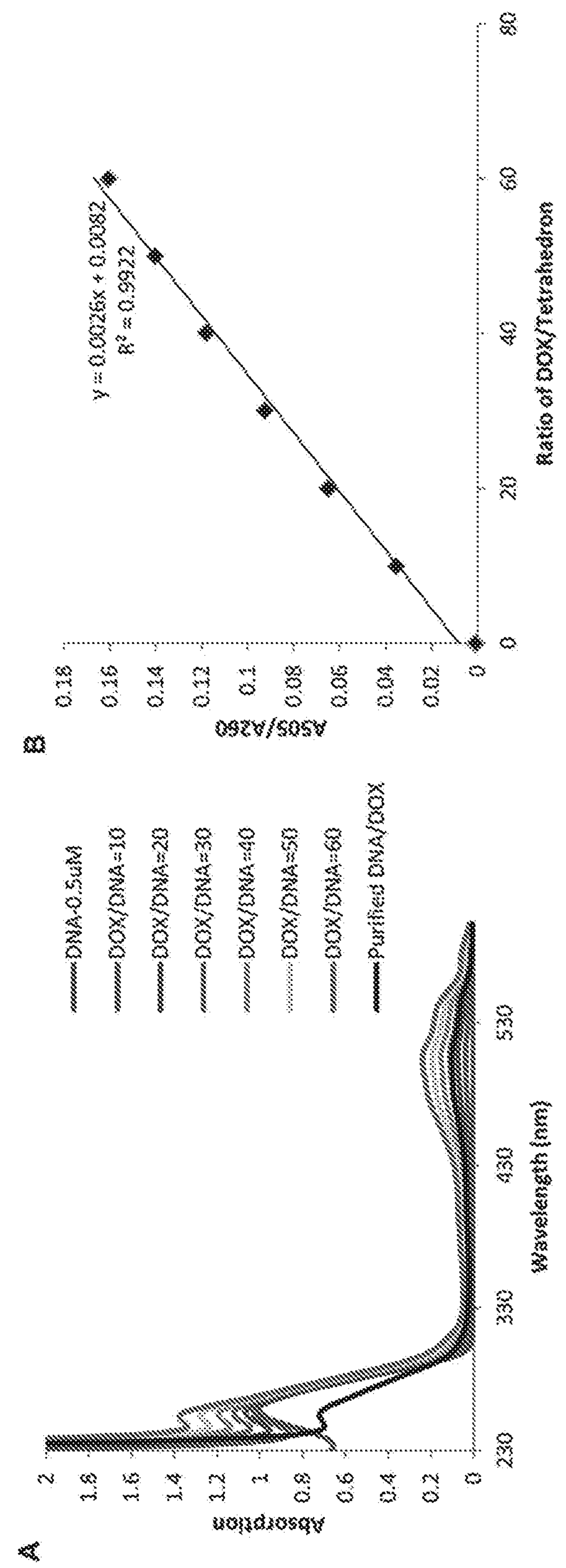
FIGS. 6A-6B shows quantification of DOX/DNA ratio in the DNA tetrahedron-DOX nanoparticle. (A) UV absorption of DNA tetrahedron (0.5 μM) after adding different amounts of DOX (5-30 μM). The excess DOX was removed through a Sephadex G-25 column for the detection samples (black line). (B) The standard curve between the $A_{505}/A_{260}$ (Y axis) and the ratio of DOX/DNA tetrahedron (X axis). The amount of DOX binding to tetrahedron in the detection sample was calculated using the equation set forth in panel B. The maximum ratio of DOX/DNA was 52.9±2.1 based on triplicate assays.

A HER2 overexpressing cell line, BT474, was used to evaluate the cell growth inhibitory activity of the DNA tetrahedron-affibody III in comparison with a commercial antibody, transtuzumab.[18] As shown in FIG. 6, III efficiently inhibited the growth of BT474 cells at 100 nM concentration, exhibiting 30% and 49% inhibition after incubation for 72 hours and 96 hours, respectively. Used as a control, the inhibition of BT474 cells by trastuzumab was not dose-dependent, consistent with a reported study.[19] The highest inhibition of BT474 cells by trastuzumab was approximately 7% over the same concentration range. This was comparable with a report in which the concentration of trastuzumab required for 30% cell growth inhibition ($IC_{30}$) was 230 nM after a 72 hour exposure.[27] The observed difference between the inhibitory activities might plausibly be due in part to stability differences for trastuzumab, which is common for antibodies. Additionally, DNA-affibody nanoparticle III has a smaller size than trastuzumab (95 vs 150 kDa), which makes it more attractive as a therapeutic candidate.

Small molecule drugs have been the preferred agents for cancer treatment for many years due to their favorable properties such as oral bioavailability, ability to cross membranes and low cost. On the other hand, small molecules also have some limitations, such as low specificity for cancer cells and frequent toxicity. An antibody-drug conjugate, such as T-DM1 can specifically target HER2 overexpressing cells.[10] However, each antibody molecule can deliver only a few molecules of the associated small molecule drug. In addition, the covalent bonds between antibody and drug limit the release of the small molecule drugs. In this study, the DNA tetrahedron nanostructure III was also used as a vehicle to deliver small molecule drugs into cancer cells. The DNA nanostructure provides a high capacity for binding small molecule anti-cancer drugs through non-covalent association.[20] Here, doxorubicin (DOX) was selected as a model drug for this purpose because of its high efficacy for treating breast, stomach, lung, ovarian, and bladder cancers, as well as its fluorescence properties. The DNA tetrahedron-affibody structure III was incubated with excess doxorubicin at room temperature for 10 minutes to obtain the DNA tetrahedron-affibody-drug nanoparticle (IV) (FIG. 1). After purification using a Sephadex G-25 column, the average number of DOX molecules in the nanoparticle was determined using UV-Vis spectrophotometry (FIGS. 7A-7B). Each DNA tetrahedron molecule bound ~53 molecules of doxorubicin. The structure of the DNA tetrahedron-affibody-drug nanoparticle (IV) was also verified using AFM microscopy (FIG. 5B). The binding of DOX did not change the structure of the DNA tetrahedron.

Figure 8:
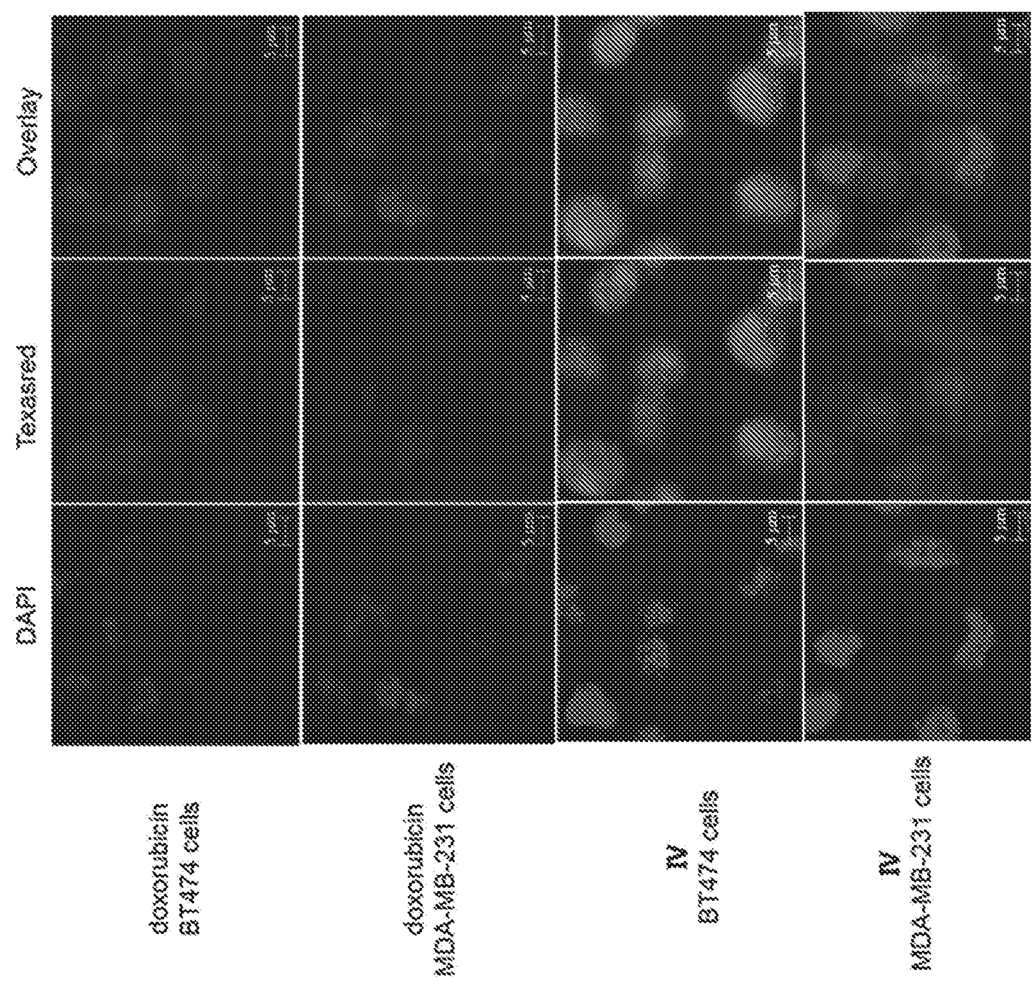
FIG. 8 demonstrates a binding assay using HER2 overexpressing cells. $HER2^+$ BT474 cancer cells and $HER2^+$ MDA-MB-231 cancer cells were incubated with doxorubicin (DOX) and a DNA tetrahedron-affibody-DOX nanoparticle (IV) for 1 hour. The fluorescent images were obtained using a fluorescence microscope (Nikon Ti-U, Japan).
Figure 9:
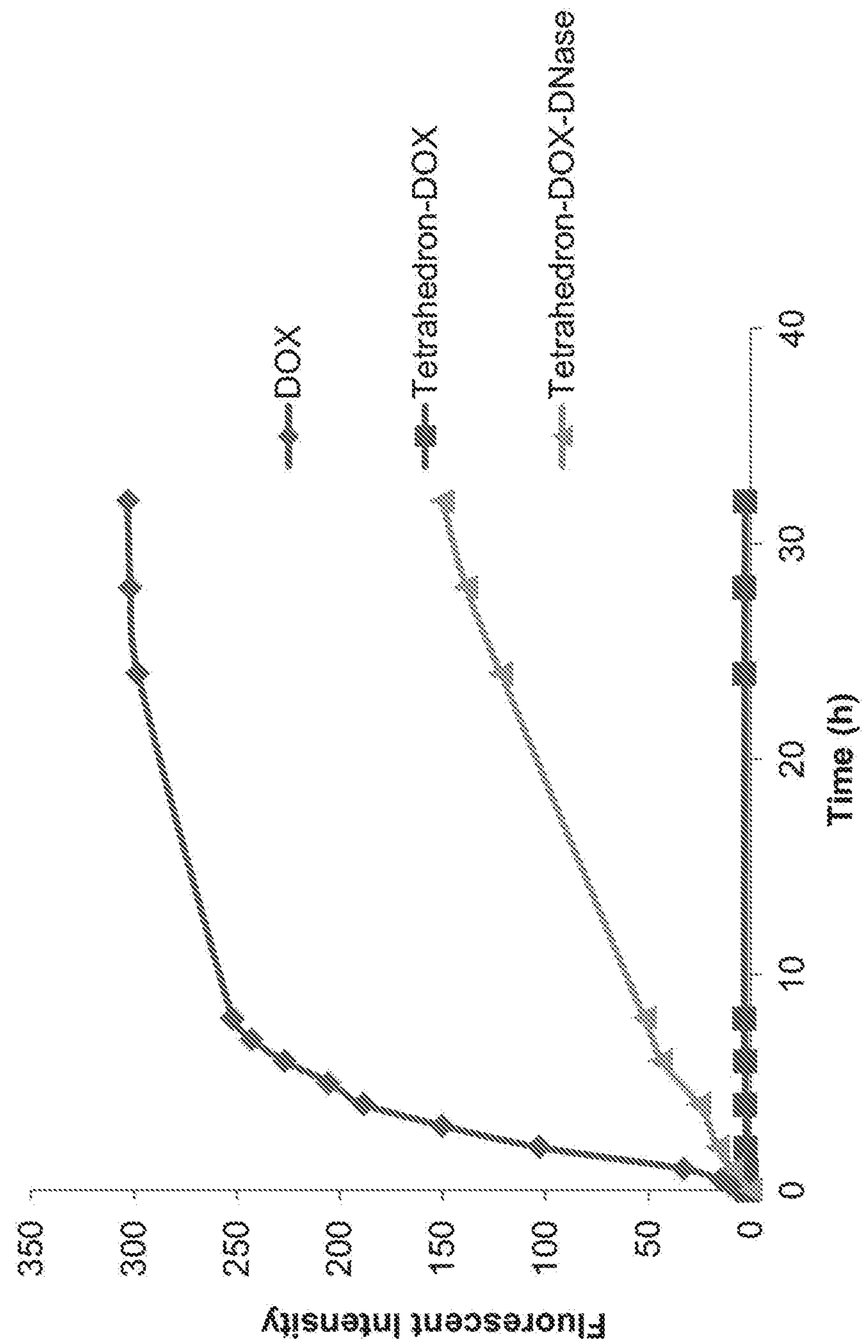
FIG. 9 is a graph presenting data from an assay of doxorubicin (DOX) release from a DNA tetrahedron-affibody-DOX nanoparticle. The fluorescence spectra of DOX were measured using a Varian Cary Eclipse Fluorescence Spectrophotometer with the excitation slit as 10 nm and emission slit as 10 nm. The samples were excited at 490 nm, and the emission spectra were recorded at the range of 510-700 nm.
Figure 10:
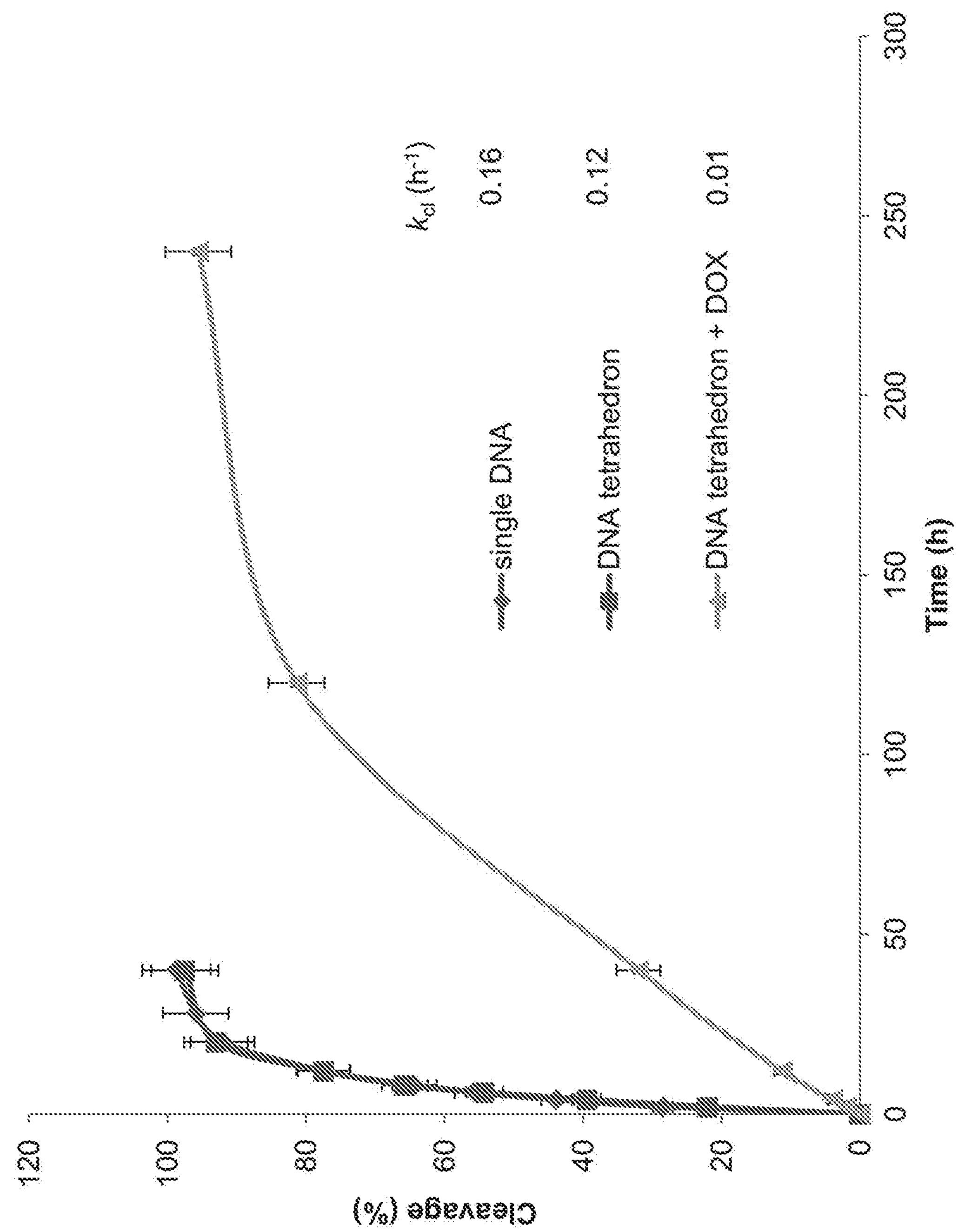
FIG. 10 is a graph presenting data from an assay testing the stability of single strand DNA and DNA tetrahedron nanoparticles in 50% fetal bovine serum. The reaction mixture was analyzed by 15% denaturing polyacrylamide gel (7 M urea). After electrophoresis in 89 mM Tris buffer, pH 8.0, containing 89 mM boric acid and 2 mM EDTA at 100 V for 1 hour, the gel was stained with ethidium bromide for 30 min and visualized using UV light. The extent of reaction (expressed as the percentage of DNA cleavage) was quantified by utilizing ImageQuant version 5.2 software.

Since the affibody binds specifically to the HER2 receptor, the DNA tetrahedron-affibody-drug nanoparticle (IV) showed a greater binding ability to HER2 overexpressing cancer cells compared to doxorubicin itself (FIG. 9). The HER2 receptor is highly overexpressed in the breast cancer cell line BT474. Comparatively, the HER2 receptor is expressed at a low level in the breast cancer cell MDA-MB-231.[18] In the binding assay, the doxorubicin itself bound to both cancer cell lines with a relatively weak ability and did not shown any selectivity between them. However, nanoparticle IV bound to HER2 overexpressing cancer cells with greater affinity and higher selectivity. It bound to the HER2 low expressing cell line MDA-MB-231 with less than two-fold enhancement compared to doxorubicin (FIG. 9 and FIG. 8). Comparatively, its affinity for the HER2 highly overexpressing cell BT474 was increased three-fold.

The DNA tetrahedron-affibody-drug nanoparticle is a highly efficient tool to deliver doxorubicin to HER2 overexpressing cancer cells specifically. The DOX binds persistently to the DNA tetrahedron-affibody nanoparticle in phosphate-buffered saline (PBS, pH 7.4). However, it is released from the nanoparticle in the presence of DNase (FIG. 8). In serum, the stability of nanoparticle IV is 16-fold higher than that of single-strand DNA (FIG. 9). In addition, the DNA tetrahedron-affibody nanoparticle III itself has a higher inhibitory activity than commercial trastuzumab. Therefore, it seems reasonable that nanoparticle IV should exhibit higher inhibitory activity to HER2 overexpressing breast cancer cells than doxorubicin and trastuzumab. As noted above, trastuzumab has very low activity in inhibiting the growth of BT474 cells. Thus, we used only doxorubicin as a control to compare its activity with that of nanoparticle IV.

As shown in FIGS. 11A-11C, doxorubicin exhibited 19%, 43%, and 44% inhibition of BT474 cell growth at 320 nM concentration after 48, 72, and 96 h, respectively. Comparatively, nanoparticle IV (1:50 III-doxorubicin) exhibited 1.4-1.8 fold higher inhibition of BT474 cells at 6.4 nM concentration (containing 320 nM doxorubicin). Cell growth inhibition by IV was 33%, 62%, and 69% after 48, 72, and 96 h treatments, respectively. At a lower concentration (160 nM doxorubicin vs 3.2 nM nanoparticle IV), the average inhibition of IV was about 2-fold higher than that of doxorubicin (22% vs 10%). However, at a higher concentration (640 nM doxorubicin vs 12.8 nM nanoparticle IV), they exhibited comparable inhibition. The inhibition of cell growth by doxorubicin was 36%, 68% and 78% after 48, 72, and 96 h treatments, respectively. Similarly, the inhibition by IV was 38%, 73%, and 82% after 48, 72, and 96 h treatments, respectively. Based on these results, it can be concluded that nanoparticle IV was more inhibitory than doxorubicin at low concentrations (IV≤12.8 nM). However, for the HER2 low expressing MDA-MB-231 cells, the inhibition was reversed. The average percent inhibition by doxorubicin was 1.0-2.3 fold higher than IV at 160 nM concentration; 1.3-2.0 fold higher than IV at 320 nM concentration; and 1.6-2.0 fold higher than IV at 640 nM concentration after 48, 72, and 96 h treatments, respectively. The results of the MDA-MB-231 cell assay also indicated that nanoparticle IV had much lower toxicity than doxorubicin in HER2 low expressing cells.

In summary, this Example demonstrates preparation of a DNA-affibody nanoparticle comprising a DNA tetrahedron and two affibody molecules (III). The DNA-affibody nanoparticle structure had a smaller size than trastuzumab, but exhibited greater inhibitory activity toward HER2 overexpressing breast cancer cells. This Example also demonstrates that this DNA-affibody nanoparticle structure effectively delivered a small molecule drug to HER2 overexpressing breast cancer cells. It had higher selectivity and higher inhibition to HER2 overexpressing cancer cells than doxorubicin. Comparatively, it had lower inhibitory activity toward HER2 low-expressing cancer cells. Accordingly, this Example demonstrates that DNA-affibody nanoparticles are good candidates for high specificity, high efficacy, and low toxicity drugs for the treatment of HER2 overexpressing breast cancers.

Example 2—Peptide-DNA-Drug Nanoparticle to Crosslink HER2$^+$ Cancer Cells and Inhibit their Metastasis This Example presents an innovative strategy to crosslink (i.e., aggregate) HER2$^+$ cancer cells using a DNA tetrahedron-affibody-drug nanoparticle that comprises four affibody molecules in the middle of four edges of a DNA tetrahedron. Crosslinking cancer cells in a primary tumor should disfavor and block metastasis at any stage of progression. The nanoparticles described in this section are structurally analogous to two covalently linked monoclonal antibody molecules and are configured to aggregate or crosslink HER2$^+$ cancer cells as illustrated in FIG. 13.

As shown in FIG. 12, tetrahedron-affibody-doxorubicin nanoparticle V comprises four affibody molecules located on four edges of a DNA tetrahedron having a total of six edges in an asymmetrical structure. Tetrahedron-affibody-doxorubicin nanoparticle VI contains four affibody molecules at its four apexes. The structure of nanoparticle VI is symmetrical and may block the metastasis of HER2$^+$ cancer cells more efficiently.

In a typical antibody-drug conjugate, such as T-DM1, each antibody molecule is covalently coupled to only a few molecules of the drug. Furthermore, covalent bonds between the drug and antibody limit the efficiency of drug release. Comparatively, the affibody-linked DNA tetrahedrons described here provide a higher capacity to deliver small molecule drugs via non-covalent association. Referring again to FIG. 12, binding the small molecule breast cancer drug, doxorubicin (DOX), to a nanoparticle by intercalation formed a DNA tetrahedron-affibody-DOX nanoparticle (nanoparticle IV). In complex IV, each nanoparticle (edge length of approximately 10 nm) bound more than 50 molecules of doxorubicin. This nanoparticle exhibited higher inhibition of BT474 in the concentration range of 3.2-12.8 nM (containing 160-640 nM DOX) than free doxorubicin itself in the same 160-640 nM concentration range. However, the nanoparticle exhibited lower inhibitory activity toward MDA-MB-231 cancer cells, which exhibit low expression of HER2. Accordingly, while nanoparticle IV had high specificity and efficacy for the treatment of HER2 overexpressing cancers. Its toxicity toward normal cells (which do not overexpress HER2) should be correspondingly diminished.

Figures 14A, 14B, 14C, 14D:
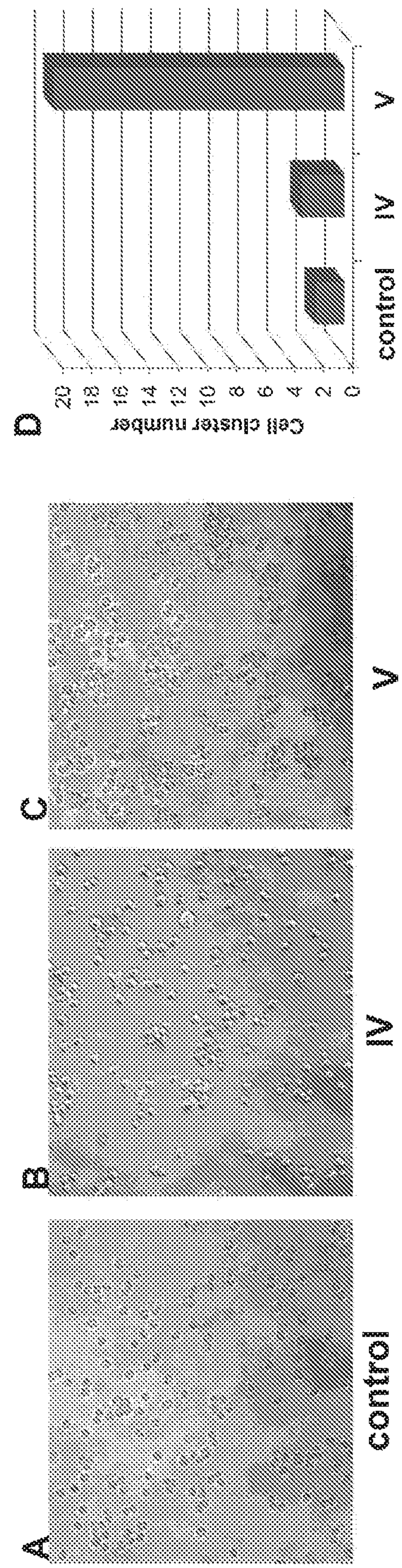

The ability of nanoparticle II of FIG. 12 to crosslink HER2 overexpressing cancer cells was verified using BT474 breast cancer cells. As shown in FIGS. 14A-14D, HER2$^+$ BT474 cells did not aggregate without (control, FIG. 14A). Nanoparticle IV contained two affibody molecules that are oriented in the same direction, and thus are more likely to bind twice to one cell than to crosslink adjacent cells. Consistent with this hypothesis, little aggregation was observed using nanopaticle IV (FIG. 14B). In comparison, nanoparticle V contained four affibody molecules, oriented in a manner intended to enhance aggregation of two adjacent cells. In the presence of nanoparticle V, significant aggregation was observed (FIG. 14C). Many BT474 breast cancer cells were crosslinked to each other, forming multiple cell clusters (>5 cells per cluster) in the presence of nanoparticle V. The cell cluster number in the nanoparticle V group was 10-fold higher than in the control group or in the group containing nanoparticle IV (FIG. 14D).

Figure 7:
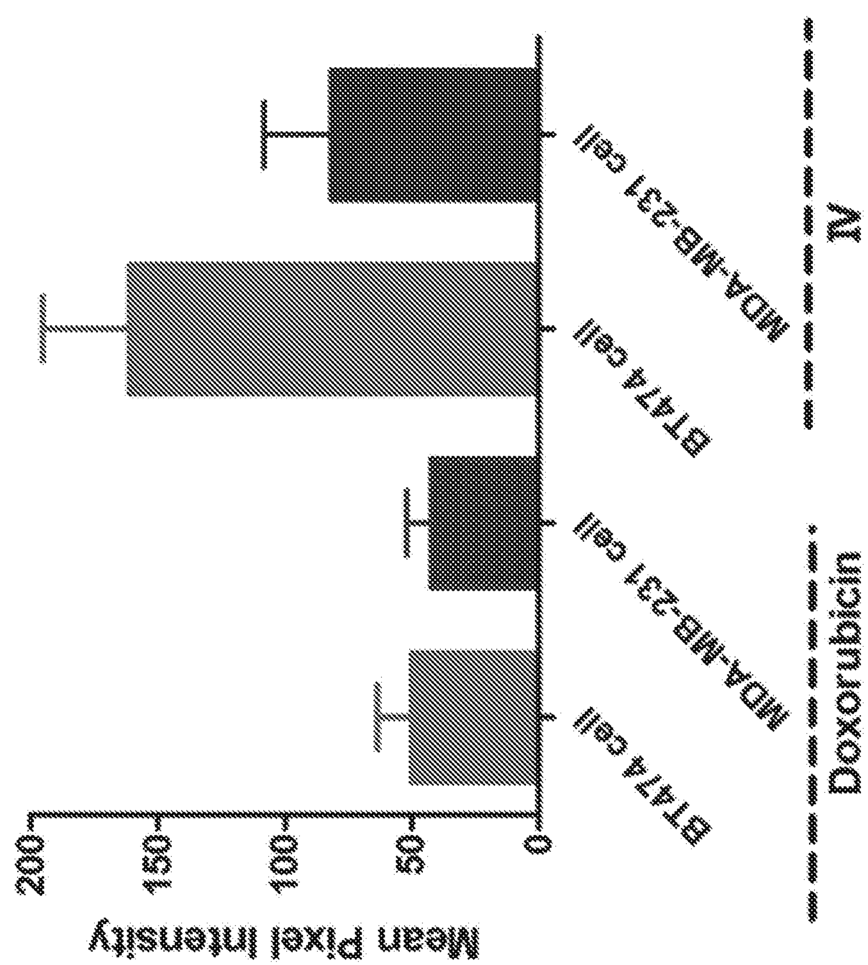
FIG. 7 is a graph presenting data quantifying the fluorescence density of doxorubicin and DNA tetrahedron-affibody-doxorubicin nanoparticle (IV) on the surface of BT474 and MDA-MB-231 cells. $HER2^+$ cancer cells of cell lines BT474 and MDA-MB-231 were incubated with doxorubicin and DNA tetrahedron-affibody-doxorubicin nanoparticle (IV) for 1 hour. The fluorescent images were obtained using a fluorescence microscope (Nikon Ti-U, Japan). The mean pixel intensity within the region of interest was calculated. The data was expressed as mean±SD.

In an MTT (3-(4,5-dimethylthiazol-2-yl)-2,5-diphenyltetrazolium bromide) tetrazolium reduction assay, inhibition of the cell growth of BT474 cells by nanoparticles IV and V was similar over the concentration range of 3-13 nM (FIG. 15A). Both nanoparticles mediated greater inhibition of the HER2 overexpressing breast cancer cells than doxorubin itself (same amount of doxorubin in the three samples). Especially at the lowest concentration (3.2 nM IV and V vs 160 nM DOX), both nanoparticles exhibited about two-fold greater inhibition toward BT474 cells than doxorubin. However, both nanoparticles also exhibited lesser inhibition of MDA-MB-231 breast cancer cells expressing HER2 at a lower level (FIG. 15B). At the higher concentration (12.8 nM IV and V vs 640 nM DOX), both nanoparticles displayed about two-fold lesser inhibition toward MDA-MB-231 cells than doxorubin. These results showed that both nanoparticles specifically target the HER2 receptor and exhibit greater efficacy in inhibiting HER2 overexpressing cancers cells than doxorubicin. HER2 specific binding by nanoparticle IV has also been verified using a fluorescence binding assay. After incubating breast cancer cells for 1 hour in the presence of doxorubin or nanoparticle IV, the fluorescence intensity on the surface of cancer cells were compared, as shown in FIG. 7. In doxorubin-treated groups, both BT474 and MDA-MB-231 cell lines exhibited a relatively weak fluorescence intensity and did not show any binding selectivity. However, nanoparticle IV bound to both HER2$^+$ breast cancer cell lines with higher affinity and greater selectivity. It bound to the HER2 highly overexpressing cell line BT474 with three-fold more efficiently than doxorubicin. Binding to the HER2 low expressing cell line, MDA-MB-231, was still enhanced two-fold compared to doxorubicin. These results indicated that the DNA-affibody-doxorubicin nanoparticles are high-efficacy, high-specificity and low-toxicity drug candidates for the treatment of HER2$^+$ cancers.

Figures 16A, 16B, 16C, 16D:
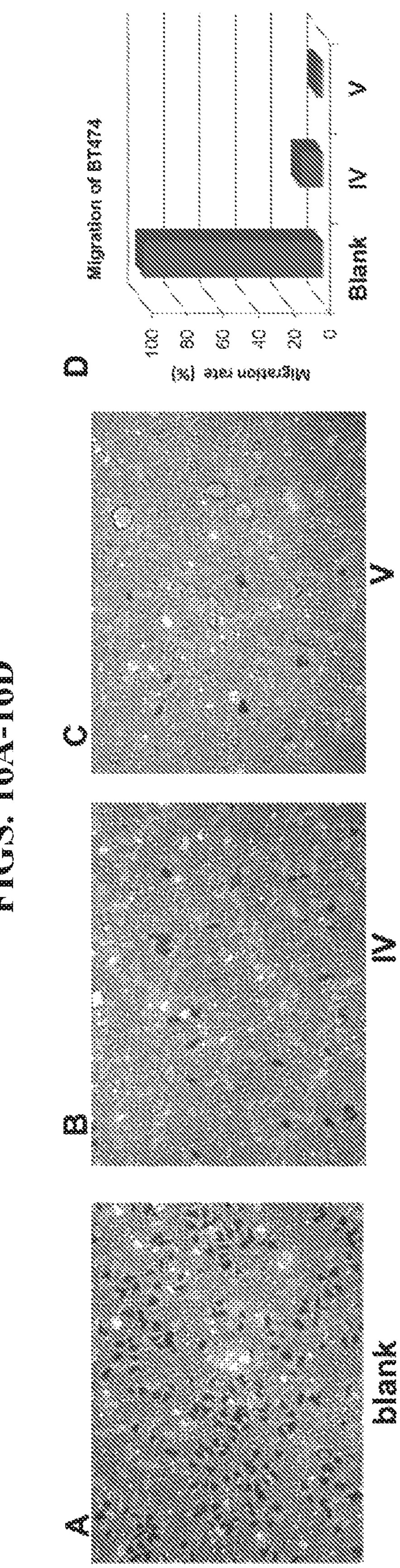
Figures 17A, 17B, 17C, 17D:
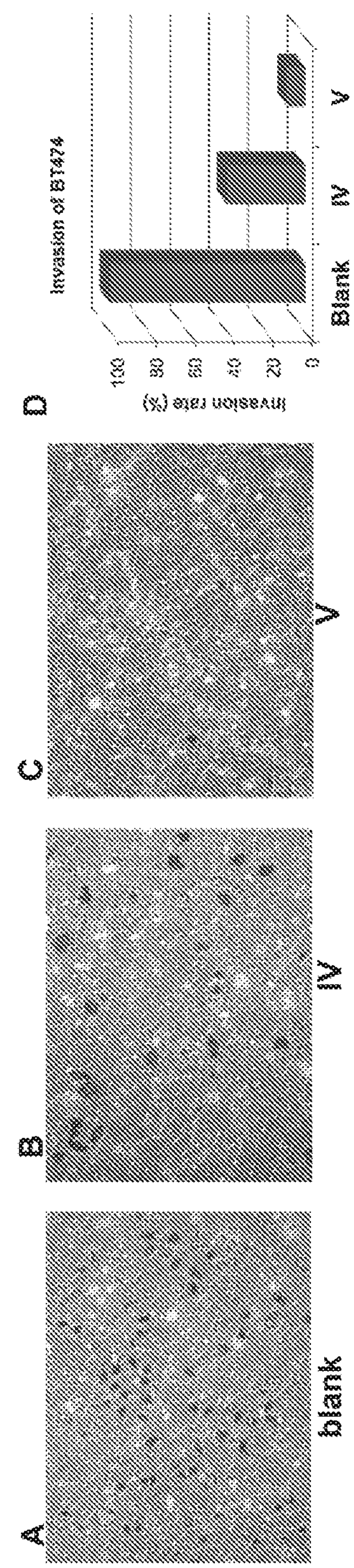

Nanoparticle II was also tested for its ability to crosslink HER2 overexpressing cancer cells to block the progression of metastasis. As shown in FIGS. 16B and 16D, nanoparticle IV inhibited the migration of BT474 cancer cells to the extent of 87% at 20 nM concentration because of its strong inhibition of cell growth (see FIG. 15A). Comparatively, nanoparticle V inhibited migration of BT474 cancer cells at the same concentration to the extent of 97% (FIGS. 16C and 16D). Since both nanoparticles exert almost the same inhibition of cell growth, the enhanced inhibition of migration by nanoparticle V is attributed to its ability to crosslink the cells. In an invasion assay using BT473 cells, a similar result was observed (FIGS. 17A-17D). Nanoparticle IV inhibited the invasion of BT474 cancer cells to the extent of 60% at 20 nM concentration but nanoparticle V inhibited invasion to the extent of 91% at the same concentration.

Lung cancer cell line, A549, which highly overexpresses HER2, was also used in the migration and invasion assays. As shown in FIGS. 18A-18B, 20 nM nanoparticle IV strongly (90%) inhibited the migration of A549 cells. In comparison, nanoparticle V inhibited the migration of A549 cells slightly more strongly (94%). At 20 nM concentration, nanoparticle IV also inhibited the invasion of A549 cancer cells (94%) while nanoparticle V inhibited invasion to the extent of 97%. Thus, both nanoparticles efficiently inhibited the migration and invasion of A549 lung cancer cells, and nanoparticle V was more efficient than nanoparticle IV.

For the cancer cells that highly overexpress HER2, nanoparticle V crosslinks them and enhances the inhibition of both migration and invasion. However, for cancer cells that overexpress HER2 less abundantly, such as MDA-MB-231, nanoparticle V has a lower potential to crosslink them. As shown in FIG. 19A, nanoparticle V had a low efficiency (16%) for inhibiting the migration of MDA-MB-231 cells. However, nanoparticle V still inhibited the invasion of MDA-MB-231 cancer cells efficiently (85%, FIG. 19B), although to the same level as cancer cells BT474 and A549 which more highly overexpress HER2.

REFERENCES

1 M. Jahanzeb, *Clin. Breast Cancer,* 2008, 8, 324-333.
2 A. Gschwind, O. M. Fischer and A. Ullrich, *Nat. Rev. Cancer,* 2004, 4, 361-370.
3 Y. Yarden and M. X. Sliwkowski, *Nat. Rev. Mol. Cell Bio.,* 2001, 2, 127-137.
4 C. L. Arteaga, M. X. Sliwkowski, C. K. Osborne, E. A. Perez, F. Puglisi and L. Gianni, *Nat. Rev. Clin. Oncol.,* 2012, 9, 16-32.
5 W. Tai, R. Mahato and K. Cheng, *J. Control. Release,* 2010, 146, 264-275.
6 F. Cappuzzo, L. Bemis and M. Varella-Garcia, *N. Engl. J. Med.,* 2006, 354, 2619-2621.

7 D. Pils, A. Pinter, J. Reibenwein, A. Alfanz, P. Horak, B. C. Schmid, L. Hefler, R. Horvat, A. Reinthaller, R. Zeillinger and M. Krainer, *Br. J. Cancer,* 2007, 96, 485-491.
8 I. Hellstrom, G. Goodman, J. Pullman, Y. Yang and K. E. Hellstrom, *Cancer Res.,* 2001, 61, 2420-2423.
9 S. Signoretti, R. Montironi, J. Manala, A. Altimari, C. Tam, G. Bubley, S. Balk, G. Thomas, I. Kaplan, L. Hlatky, P. Hahnfeldt, P. Kantoff and M. Loda, *J. Natl. Cancer Inst.,* 2000, 92, 1918-1925.
10 J. M. Lambert and R. V. Chari, *J. Med. Chem.,* 2014, 57, 6949-6964.
11 A. S. Walsh, H. Yin, C. M. Erben, M. J. A. Wood and A. J. Turberfield, *ACS Nano,* 2011, 5, 5427-5432.
12 C. M. Erben, R. P. Goodman and A. J. Turberfield, *Angew. Chem. Int. Ed.,* 2006, 45, 7414-7417.
13 S. Dou, J. Virostko, D. L. Greiner, A. C. Powers and G. Liu, *Nucleosides Nucleotides Nucleic Acids,* 2015, 34, 69-78.
14 S. Chen, L. Wang, N. E. Fahmi, S. J. Benkovic and S. M. Hecht, *J. Am. Chem. Soc.,* 2012, 134, 18883-18885.
15 S. Chen, N. E. Fahmi, L. Wang, C. Bhattacharya, S. J. Benkovic and S. M. Hecht, *J. Am. Chem. Soc.,* 2013, 135, 12924-12927.
16 S. Chen, Y. Zhang and S. M. Hecht, *Biochemistry,* 2011, 50, 9340-9351.
17 S. Chen and S. M. Hecht, *Bioorg. Med. Chem.,* 2008, 16, 9023-9031.
18 K. Subik, J. F. Lee, L. Baxter, T. Strzepek, D. Costello, P. Crowley, L. Xing, M. C. Hung, T. Bonfiglio, D. G. Hicks and P. Tang, *Breast Cancer Basic Clin. Res.,* 2010, 4, 35-41.
19 S. Ropero, J. A. Menendez, A. Vazquez-Martin, S. Montero, H. Cortes-Funes and R. Colomer, *Breast Cancer Res. Treat.,* 2004, 86, 125-137.
20 D. Agudelo, P. Bourassa, G. Berube and H. A. Tajmir-Riahi, *Int. J. Biol. Macromol,* 2014, 66, 144-150.

What is claimed is:

1. A peptide-polynucleotide chimera comprising one or more human epidermal growth factor receptor (HER) binding peptides, a linker, and a single-stranded polynucleotide, wherein at least one of the one or more HER binding peptides is an affibody comprising amino acid sequence SEQ ID NO:5.

2. The chimera of claim 1, wherein the single-stranded DNA polynucleotide has a length of 10 bases to 1000 bases.

3. The chimera of claim 1, wherein the polynucleotide is SEQ ID NO:1.

* * * * *

SEQUENCE LISTING

```
<160> NUMBER OF SEQ ID NOS: 11

<210> SEQ ID NO 1
<211> LENGTH: 63
<212> TYPE: DNA
<213> ORGANISM: Artificial Sequence
<220> FEATURE:
<223> OTHER INFORMATION: DNA1

<400> SEQUENCE: 1

aggcagttga gacgaacatt cctaagtctg aaatttatca cccgccatag tagacgtatc     60

acc                                                                   63


<210> SEQ ID NO 2
<211> LENGTH: 63
<212> TYPE: DNA
<213> ORGANISM: Artificial Sequence
<220> FEATURE:
<223> OTHER INFORMATION: DNA2

<400> SEQUENCE: 2

cctcgcatga ctcaactgcc tggtgatacg aggatgggca tgctcttccc gacggtattg     60

gac                                                                   63


<210> SEQ ID NO 3
<211> LENGTH: 63
<212> TYPE: DNA
<213> ORGANISM: Artificial Sequence
<220> FEATURE:
<223> OTHER INFORMATION: DNA3

<400> SEQUENCE: 3

cttgctacac gattcagact taggaatgtt cgacatgcga gggtccaata ccgacgatta     60

cag                                                                   63


<210> SEQ ID NO 4
<211> LENGTH: 63
<212> TYPE: DNA
<213> ORGANISM: Artificial Sequence
<220> FEATURE:
<223> OTHER INFORMATION: DNA4

<400> SEQUENCE: 4

ggtgataaaa cgtgtagcaa gctgtaatcg acgggaagag catgcccatc cactactatg     60
```

gcg 63

<210> SEQ ID NO 5
<211> LENGTH: 71
<212> TYPE: PRT
<213> ORGANISM: Artificial Sequence
<220> FEATURE:
<223> OTHER INFORMATION: HER2 affibody

<400> SEQUENCE: 5

```
Met Ile His His His His His His Leu Gln Val Asp Asn Lys Phe Asn
1               5                   10                  15

Lys Glu Met Arg Asn Ala Tyr Trp Glu Ile Ala Leu Leu Pro Asn Leu
            20                  25                  30

Asn Asn Gln Gln Lys Arg Ala Phe Ile Arg Ser Leu Tyr Asp Asp Pro
        35                  40                  45

Ser Gln Ser Ala Asn Leu Leu Ala Glu Ala Lys Lys Leu Asn Asp Ala
    50                  55                  60

Gln Ala Pro Lys Val Asp Cys
65                  70
```

<210> SEQ ID NO 6
<211> LENGTH: 63
<212> TYPE: DNA
<213> ORGANISM: Artificial Sequence
<220> FEATURE:
<223> OTHER INFORMATION: DNA5

<400> SEQUENCE: 6
caactgccta gacgaacatt cctaagtctg aaatttatca cccgccatag tagacgtatc 60
acc 63

<210> SEQ ID NO 7
<211> LENGTH: 63
<212> TYPE: DNA
<213> ORGANISM: Artificial Sequence
<220> FEATURE:
<223> OTHER INFORMATION: DNA6

<400> SEQUENCE: 7
cctcgcatga ctaggcagtt gggtgatacg aggatgggca tgctcttccc gacggtattg 60
gac 63

<210> SEQ ID NO 8
<211> LENGTH: 63
<212> TYPE: DNA
<213> ORGANISM: Artificial Sequence
<220> FEATURE:
<223> OTHER INFORMATION: DNA7

<400> SEQUENCE: 8
tgtagcaagc gattcagact taggaatgtt cgacatgcga gggtccaata ccgacgatta 60
cag 63

<210> SEQ ID NO 9
<211> LENGTH: 63
<212> TYPE: DNA
<213> ORGANISM: Artificial Sequence
<220> FEATURE:
<223> OTHER INFORMATION: DNA8

<400> SEQUENCE: 9

-continued

```
ggtgataaaa cgcttgctac actgtaatcg acgggaagag catgcccatc cactactatg     60

gcg                                                                   63


<210> SEQ ID NO 10
<211> LENGTH: 61
<212> TYPE: PRT
<213> ORGANISM: Artificial Sequence
<220> FEATURE:
<223> OTHER INFORMATION: affibody

<400> SEQUENCE: 10

Val Asp Asn Lys Phe Asn Lys Glu Met Arg His Ala Tyr Trp Glu Ile
1               5                   10                  15

Val Lys Leu Pro Asn Leu Asn Pro Arg Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys Val Asp Cys
    50                  55                  60


<210> SEQ ID NO 11
<211> LENGTH: 61
<212> TYPE: PRT
<213> ORGANISM: Artificial Sequence
<220> FEATURE:
<223> OTHER INFORMATION: affibody

<400> SEQUENCE: 11

Val Asp Asn Lys Phe Asn Lys Glu Leu Arg Gln Ala Tyr Trp Glu Ile
1               5                   10                  15

Gln Ala Leu Pro Asn Leu Asn Trp Thr Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys Val Asp Cys
    50                  55                  60
```